(12) United States Patent
Suzuki et al.

(10) Patent No.: US 9,714,193 B2
(45) Date of Patent: Jul. 25, 2017

(54) FLOAT GLASS FOR CHEMICAL STRENGTHENING

(71) Applicant: ASAHI GLASS COMPANY, LIMITED, Tokyo (JP)

(72) Inventors: Yuichi Suzuki, Tokyo (JP); Tetsuya Nakashima, Tokyo (JP); Jun Sasai, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/753,416

(22) Filed: Jun. 29, 2015

(65) Prior Publication Data
US 2016/0023945 A1 Jan. 28, 2016

Related U.S. Application Data

(63) Continuation of application No. PCT/JP2013/085125, filed on Dec. 27, 2013.

(30) Foreign Application Priority Data

Dec. 27, 2012 (JP) .................................. 2012-285511

(51) Int. Cl.
| | | |
|---|---|---|
| *C03C 21/00* | (2006.01) | |
| *C03C 3/087* | (2006.01) | |
| *C03B 18/18* | (2006.01) | |
| *C03B 18/20* | (2006.01) | |
| *C03B 25/08* | (2006.01) | |
| *C03B 18/02* | (2006.01) | |
| *G01N 23/223* | (2006.01) | |
| *G01N 23/225* | (2006.01) | |
| *C03C 23/00* | (2006.01) | |

(52) U.S. Cl.
CPC ............ *C03C 21/005* (2013.01); *C03B 18/02* (2013.01); *C03B 18/18* (2013.01); *C03B 18/20* (2013.01); *C03B 25/08* (2013.01); *C03C 3/087* (2013.01); *C03C 21/002* (2013.01); *C03C 23/008* (2013.01); *G01N 23/223* (2013.01); *G01N 23/2258* (2013.01); *Y02P 40/57* (2015.11)

(58) Field of Classification Search
None
See application file for complete search history.

(56) References Cited

U.S. PATENT DOCUMENTS

| | | | | |
|---|---|---|---|---|
| 3,473,908 A | * | 10/1969 | Snow ...................... | C03B 18/02 65/157 |
| 5,093,196 A | | 3/1992 | Hecq et al. | |
| 5,292,354 A | * | 3/1994 | Hecq ...................... | C03C 21/00 65/30.1 |
| 5,643,349 A | | 7/1997 | Piper et al. | |
| 6,349,569 B1 | | 2/2002 | Piper et al. | |
| 2002/0007652 A1 | | 1/2002 | Piper et al. | |
| 2009/0253567 A1 | * | 10/2009 | Nagai ..................... | C03B 18/20 501/70 |
| 2011/0071012 A1 | | 3/2011 | Kondo et al. | |
| 2012/0196110 A1 | * | 8/2012 | Murata ................... | C03B 25/08 428/220 |
| 2012/0238435 A1 | * | 9/2012 | Arai ....................... | C03C 23/008 501/70 |
| 2013/0034670 A1 | | 2/2013 | Hashimoto et al. | |

FOREIGN PATENT DOCUMENTS

| | | | | |
|---|---|---|---|---|
| JP | 61205641 A | * | 9/1986 | |
| JP | 61-236635 | | 10/1986 | |
| JP | 63-159238 | | 7/1988 | |
| JP | 7-72093 | | 8/1995 | |
| JP | 9-501647 | | 2/1997 | |
| JP | 11-278875 | | 10/1999 | |
| JP | 2000-268349 A | | 9/2000 | |
| JP | 2004-131314 A | | 4/2004 | |
| JP | 2005055669 A | * | 3/2005 | |
| JP | 2007204295 A | * | 8/2007 | |
| JP | 2011-084456 A | | 4/2011 | |
| JP | 2011-201711 A | | 10/2011 | |
| JP | 2012-203941 A | | 10/2012 | |
| JP | 2012-216276 A | | 11/2012 | |
| JP | 2012-236737 | | 12/2012 | |
| JP | WO 2013005588 A1 | * | 1/2013 | ........... C03C 21/006 |
| JP | WO 2013005608 A1 | * | 1/2013 | ........... C03C 21/087 |
| WO | WO 95/05348 | | 2/1995 | |
| WO | WO 2011/068225 | | 6/2011 | |
| WO | WO 2011/145662 A1 | | 11/2011 | |

OTHER PUBLICATIONS

International Search Report issued Apr. 8, 2014, in PCT/JP2013/085125 filed Dec. 27, 2013.

* cited by examiner

*Primary Examiner* — David Sample
(74) *Attorney, Agent, or Firm* — Oblon, McClelland, Maier & Neustadt, L.L.P.

(57) ABSTRACT

The present invention relates to a float glass for chemical strengthening, containing a bottom surface coming into contact with a molten metal at the time of forming and a top surface opposing the bottom surface, in which a difference $\Delta(N-Na_2O^2)$ determined by subtracting a square of a normalized $Na_2O$ surface concentration of the bottom surface which is a value obtained by dividing an $Na_2O$ concentration in the bottom surface by an $Na_2O$ concentration at a depth position of 100 μm therefrom, from a square of a normalized $Na_2O$ surface concentration of the top surface which is a value obtained by dividing an $Na_2O$ concentration in the top surface by an $Na_2O$ concentration at a depth position of 100 μm therefrom, is 0.040 or less.

18 Claims, 16 Drawing Sheets

Fig. 4
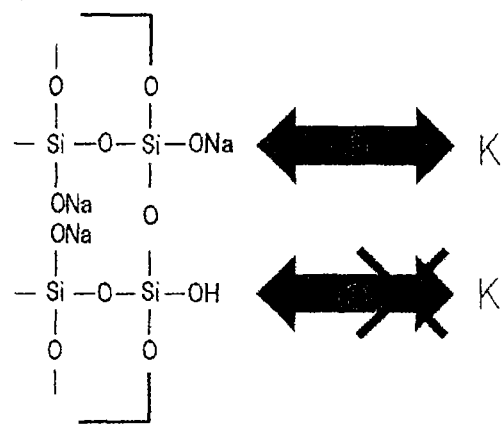
① Governed by Entropy
Si—ONa + KNO$_3$ → Si—OK + NaNO$_3$
② Governed by Enthalpy
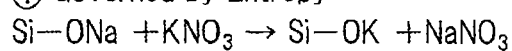
(Weak Acid)                    (Strong Acid)

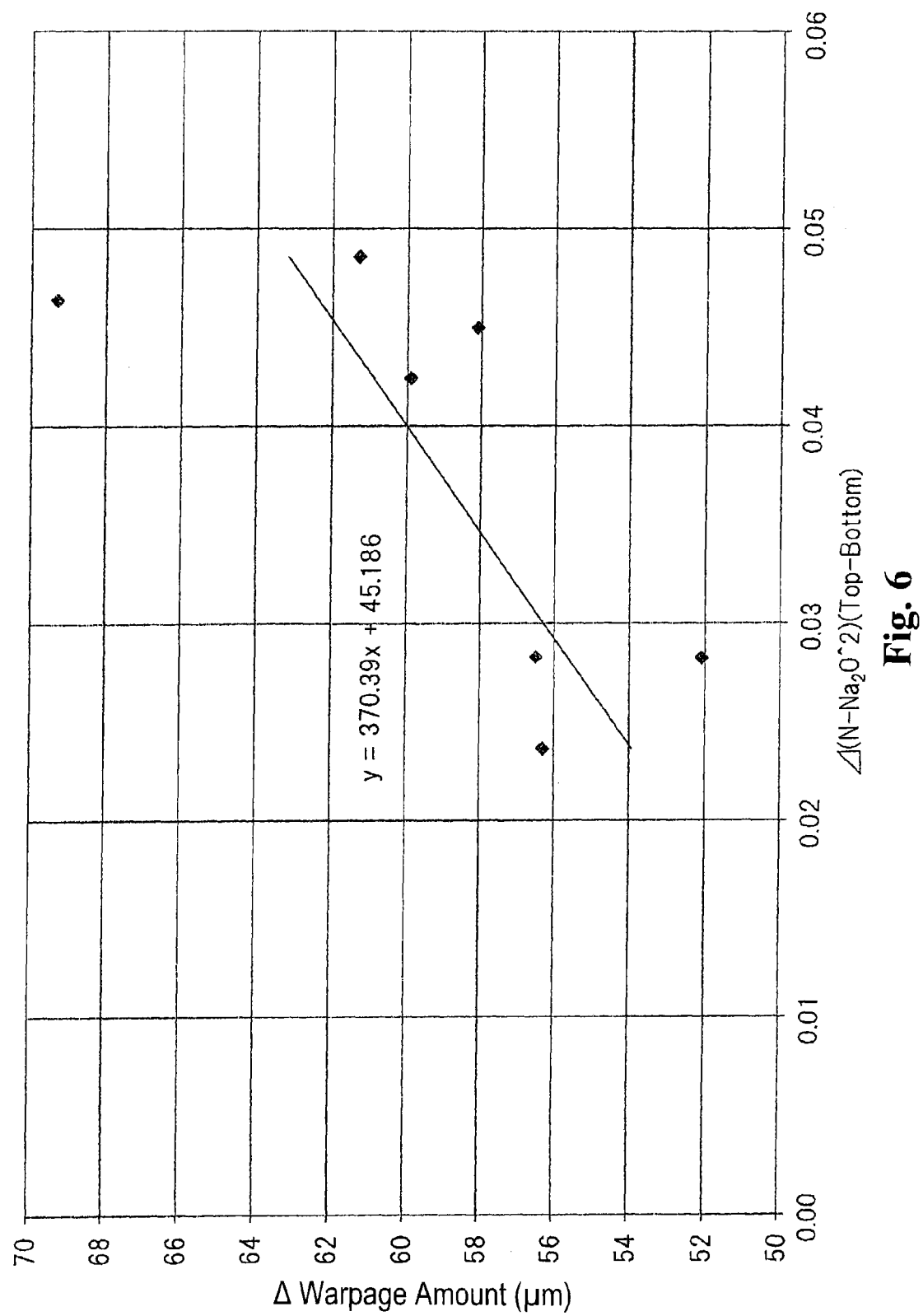

Fig. 10
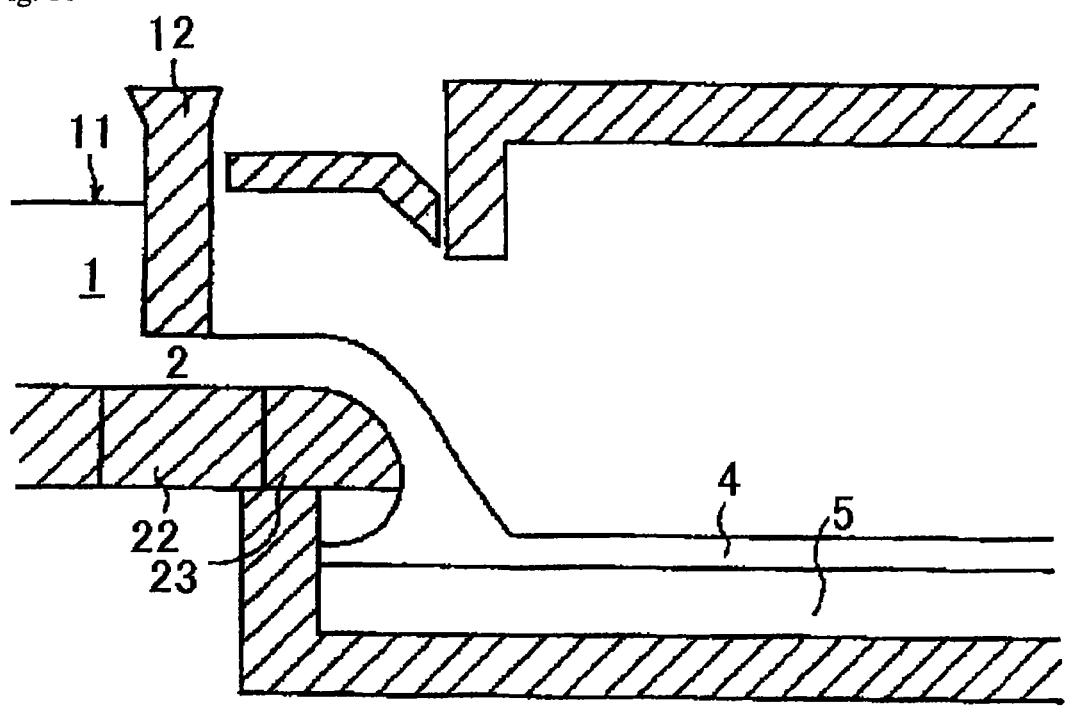
Fig. 11
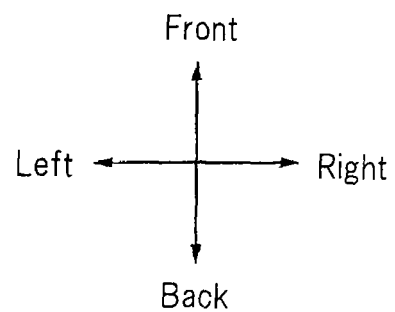
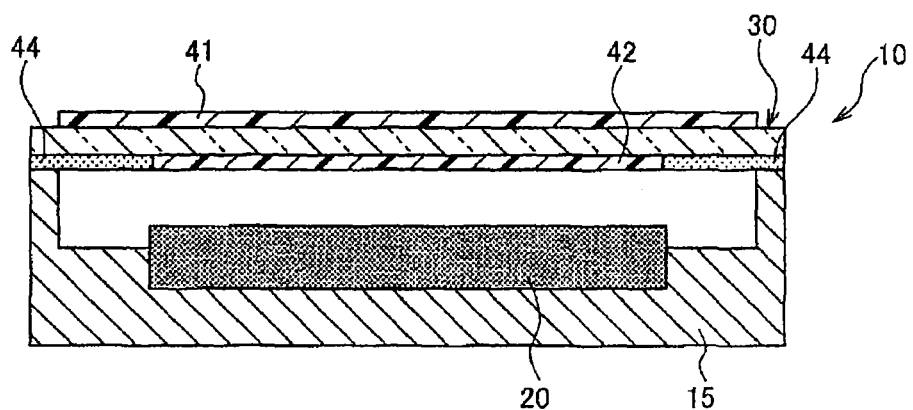

FLOAT GLASS FOR CHEMICAL STRENGTHENING

TECHNICAL FIELD

The present invention relates to a float glass for chemical strengthening.

BACKGROUND ART

Recently, in a flat panel display device such as mobile phone or personal digital assistant (PDA), a thin sheet-like cover glass is disposed on a front surface of a display to extend in a wider region than the image display area with an aim to enhance the protection and beauty of the display.

Such the flat panel display device is required to be lightweight and thin and in order to meet this requirement, the thickness of a cover glass used for display protection is also required to be reduced.

However, decreasing the thickness of the cover glass causes the problems that the strength is reduced and the cover glass itself may be broken by dropping, etc. during use or carrying and therefore its primary role of protecting the display device cannot be fulfilled.

Accordingly, in the conventional cover glass, with an aim to improve the scratch resistance, a compressive stress layer is formed on the surface by chemically strengthening a float glass produced by a float method, and the scratch resistance of the cover glass is thereby enhanced.

It has been reported that warpage occurs in a float glass after chemical strengthening and impairs the flatness (Patent Document 1). The warpage is thought to occur due to the difference in the chemical strengthening behavior between a glass surface (hereinafter, also referred to as top surface) that is out of contact with molten tin at the time of float forming, and a glass surface (hereinafter, also referred to as bottom surface) that comes into contact with molten tin.

Heretofore, the reason for the difference in the chemical strengthening behaviors between the top surface of the float glass and the bottom surface has been considered to be the invasion of a molten metal into the glass surface in contact with the molten metal at the time of float forming (Patent Document 1).

In Patent Document 1, it is disclosed that the warpage is improved when a sheet-like material produced by a float method and processed is, without applying surface polishing, dipped in or put into contact with Li ion, Na ion or a mixed inorganic salt thereof and then chemically strengthened.

Furthermore, in order to reduce the warpage, conventionally employed is a coping method of decreasing the strengthening stress produced by chemical strengthening or performing chemical strengthening after subjecting the top surface and the bottom surface of a float glass to a grinding treatment, a polishing treatment, etc. so as to remove a surface heterogeneous layer.

PRIOR ART DOCUMENT

Patent Document

Patent Document 1: Japanese Patent No. 2,033,034

SUMMARY OF THE INVENTION

Problems that the Invention is to Solve

However, in the method described in Patent Document 1, the float glass needs to be dipped in a mixed inorganic salt before chemical strengthening, and this is cumbersome. In addition, the method of decreasing the strengthening stress may afford insufficient strength to the float glass after chemical strengthening.

Furthermore, the method of subjecting the top surface and the bottom surface of a float glass to a grinding treatment, a polishing treatment, etc. before chemical strengthening has a problem from the standpoint of enhancing the productivity, and it is preferable to omit such the grinding treatment, the polishing treatment, etc.

Accordingly, an object of the present invention is to provide a float glass for chemical strengthening, which can effectively suppress the warpage after chemical strengthening.

Means for Solving the Problems

The present inventors have found that the main cause of warpage occurring due to the difference in the chemical strengthening behaviors between the bottom surface and the top surface when chemically strengthening a soda-lime glass produced by a float process is not necessarily a metal invading a glass surface in contact with the molten metal at the time of float forming but is the difference in the weathering degree between the top surface and the bottom surface, namely, the difference in the degree of hydration-dealkalization.

Furthermore, they found that by suppressing the effect thereof, the strengthening degree in chemical strengthening can be equalized between the top surface and the bottom surface and therefore the warpage of a float glass after chemical strengthening can be reduced. In addition, they found that the weathering has a profound effect particularly in a low DOL region where the depth of compressive stress layer (DOL) is typically 20 μm or less, 15 μm or less or 10 μm or less, and by diminishing the effect of weathering degree in this region, the warpage of a float glass after chemical strengthening can be effectively reduced. They have accomplished the present invention based on these findings.

The present invention is as the following.

1. A float glass for chemical strengthening, containing a bottom surface coming into contact with a molten metal at the time of forming and a top surface opposing the bottom surface, in which a difference $\Delta(N-Na_2O^2)$ determined by subtracting a square of a normalized $Na_2O$ surface concentration of the bottom surface which is a value obtained by dividing an $Na_2O$ concentration in the bottom surface by an $Na_2O$ concentration at a depth position of 100 μm therefrom, from a square of a normalized $Na_2O$ surface concentration of the top surface which is a value obtained by dividing an $Na_2O$ concentration in the top surface by an $Na_2O$ concentration at a depth position of 100 μm therefrom, is 0.040 or less, where each $Na_2O$ concentration is a value measured by a fluorescent X-ray analysis using an Na-Kα ray.

A float glass for chemical strengthening, containing a bottom surface coming into contact with a molten metal at the time of forming and a top surface opposing the bottom surface, in which a Δion exchange amount 1 which is a value obtained by subtracting an ion exchange amount 1 in the bottom surface from an ion exchange amount 1 in the top surface is 0.32 or less, where the ion exchange amount 1 is a value determined according to the following formula (2-1):

Ion exchange amount 1=5.51×(normalized $Na_2O$ surface concentration)−0.038×(Sn concentration) formula (2-1)

in formula (2-1), the normalized $Na_2O$ surface concentration is a value obtained by dividing an $Na_2O$ concentration at the surface by an $Na_2O$ concentration at a depth position of 100 μm, where the $Na_2O$ concentration is a value measured by a fluorescent X-ray analysis using an Na-Kα ray; and the Sn concentration is an Sn deposition amount (unit: as $SnO_2$μg/$cm^2$) per unit area of the top surface and the bottom surface. In the present specification, the unit of the Sn deposition amount per unit area is indicated as "as $SnO_2$μg/$cm^2$" in order to specify that the Sn deposition amount per unit area is expressed by a deposition mass in terms of $SnO_2$ per 1 $cm^2$ when Sn is assumed to exist in the form of $SnO_2$. In the present specification, the Sn deposition amount (unit: μg/$cm^2$) per unit area possesses the same meaning as the Sn deposition amount (unit: as $SnO_2$μg/$cm^2$) per unit area.

3. A float glass for chemical strengthening, containing a bottom surface coming into contact with a molten metal at the time of forming and a top surface opposing the bottom surface, in which W1 determined according to the following formula (3-1) is 56 or less:

$$W1=-16\times(\Delta H/Si)-6.47\times(Sn\ concentration\ difference)-43.8\times(\Delta ion\ exchange\ amount\ 1) \quad \text{formula (3-1)}$$

in formula (3-1), the ΔH/Si is a value obtained by subtracting a normalized hydrogen concentration in the bottom surface from a normalized hydrogen concentration in the top surface, where the normalized hydrogen concentration is a value obtained by dividing an average hydrogen concentration at a depth of 0 to 10 μm by an average hydrogen concentration at a depth of 105 to 110 μm, in which the average hydrogen concentration at a depth of 0 to 10 μm and the average hydrogen concentration at a depth of 105 to 110 μm are values measured under the following analysis conditions:

(Analysis Conditions)

Measurement apparatus: secondary ion mass spectrometry apparatus with a quadrupole mass spectrometer Primary ion species: $Cs^+$
Primary accelerating voltage: 5.0 kV
Primary ion current: 1 μA
Primary ion incident angle (angle from direction perpendicular to sample surface): 60°
Luster size: 200×200 μm$^2$
Detection region: 40×40 μm$^2$
Secondary ion polarity: minus
Electron gun for neutralization: used;

in formula (3-1), the Sn concentration difference is a difference obtained by subtracting an Sn deposition amount (unit: μg/$cm^2$) per unit area of the top surface from an Sn deposition amount (unit: as $SnO_2$μg/$cm^2$) per unit area of the bottom surface, and in the case where the glass does not contain $SnO_2$, this is equivalent to the Sn deposition amount per unit area of the bottom surface; and in formula (3-1), the Δion exchange amount 1 is a value obtained by subtracting an ion exchange amount 1 in the bottom surface from an ion exchange amount 1 in the top surface, where the ion exchange amount 1 is determined according to the following formula:

$$\text{Ion exchange amount } 1=5.51\times(\text{normalized } Na_2O\ \text{surface concentration})-0.038\times(\text{Sn concentration})$$

in which the normalized $Na_2O$ surface concentration is a value obtained by dividing an $Na_2O$ concentration at the surface by an $Na_2O$ concentration at a depth position of 100 where the $Na_2O$ concentration is a value measured by a fluorescent X-ray analysis using an Na-Kα ray.

4. A float glass for chemical strengthening, containing a bottom surface coming into contact with a molten metal at the time of forming and a top surface opposing the bottom surface, in which an absolute value of W2 determined according to the following formula (4-1) is 56 or less:

$$W2=9.18\times\Delta[(\text{ion exchange amount})/(\text{H/Si})]+49 \quad \text{formula (4-1)}$$

in formula (4-1), the Δ[(ion exchange amount)/(H/Si)] is a value determined by subtracting a value obtained by dividing an ion exchange amount 1 in the bottom surface by a normalized hydrogen concentration H/Si in the same surface, from a value obtained by dividing an ion exchange amount 1 in the top surface by a normalized hydrogen concentration H/Si in the same surface, where the ion exchange amount 1 is determined according to the following formula:

$$\text{Ion exchange amount } 1=5.51\times(\text{normalized } Na_2O\ \text{surface concentration})-0.038\times(\text{Sn concentration})$$

in the formula, the normalized $Na_2O$ surface concentration is a value obtained by dividing an $Na_2O$ concentration at the surface by an $Na_2O$ concentration at a depth position of 100 μm, where the $Na_2O$ concentration is a value measured by a fluorescent X-ray analysis using an Na-Kα ray, and the Sn concentration is an Sn deposition amount (unit: as $SnO_2$μg/$cm^2$) per unit area of the top surface and the bottom surface;

and where the normalized hydrogen concentration is a value obtained by dividing an average hydrogen concentration at a depth of 0 to 10 μm by an average hydrogen concentration at a depth of 105 to 110 μm, in which the average hydrogen concentration at a depth of 0 to 10 μm and the average hydrogen concentration at a depth of 105 to 110 μm are values measured under the following analysis conditions:

(Analysis Conditions)

Measurement apparatus: secondary ion mass spectrometry apparatus with a quadrupole mass spectrometer Primary ion species: $Cs^+$
Primary accelerating voltage: 5.0 kV
Primary ion current: 1 μA
Primary ion incident angle (angle from direction perpendicular to sample surface): 60°
Luster size: 200×200 μm$^2$
Detection region: 40×40 μm$^2$
Secondary ion polarity: minus
Electron gun for neutralization: used.

5. The float glass for chemical strengthening according to any one of the above 1 to 4, containing a bottom surface coming into contact with a molten metal at the time of forming and a top surface opposing the bottom surface, in which W3 determined according to the following formula (5-1) is 58 or less:

$$W3=744\times[(\Delta N-Na_2O)+0.01\times(\text{Sn concentration difference})] \quad \text{formula (5-1)}$$

in formula (5-1), the $\Delta N-Na_2O$ is a value determined by subtracting a normalized $Na_2O$ surface concentration of the bottom surface which is a value obtained by dividing an $Na_2O$ concentration at the surface in the bottom surface by an $Na_2O$ concentration at a depth position of 100 μm therefrom, from the normalized $Na_2O$ surface concentration of the top surface which is a value obtained by dividing an $Na_2O$ concentration at the surface in the top surface by an $Na_2O$ concentration at a depth position of 100 μm therefrom, where each $Na_2O$ concentration is a value measured by a fluorescent X-ray analysis using an Na-Kα ray; and in formula (5-1), the Sn concentration difference is a difference obtained by subtracting an Sn deposition amount (unit: as $SnO_2 \mu g/cm^2$) per unit area of the top surface from an Sn deposition amount (unit: as $SnO_2 \mu g/cm^2$) per unit area of the bottom surface, and in the case where the glass does not contain $SnO_2$, this is equivalent to the Sn deposition amount per unit area of the bottom surface.

6. The float glass for chemical strengthening according to any one of the above 1 to 4, containing a bottom surface coming into contact with a molten metal at the time of forming and a top surface opposing the bottom surface, in which Δion exchange amount 2 which is a value obtained by subtracting an ion exchange amount 2 in the bottom surface from an ion exchange amount 2 in the top surface is 0.33 or less, where the ion exchange amount 2 is a value determined according to the following formula (6-1):

Ion exchange amount 2=−0.02×(H/Si)+5.54×(N—$Na_2O$ concentration)−0.037×(Sn concentration)  formula (6-1)

in formula (6-1), the H/Si is a normalized hydrogen concentration, where the normalized hydrogen concentration is a value obtained by dividing an average hydrogen concentration at a depth of 0 to 10 μm by an average hydrogen concentration at a depth of 105 to 110 μm, in which the average hydrogen concentration at a depth of 0 to 10 μm and the average hydrogen concentration at a depth of 105 to 110 μm are values measured under the following analysis conditions:

(Analysis Conditions)

Measurement apparatus: secondary ion mass spectrometry apparatus with a quadrupole mass spectrometer Primary ion species: $Cs^+$
Primary accelerating voltage: 5.0 kV
Primary ion current: 1 μA
Primary ion incident angle (angle from direction perpendicular to sample surface): 60°
Luster size: 200×200 μm$^2$
Detection region: 40×40 μm$^2$
Secondary ion polarity: minus
Electron gun for neutralization: used;

and in formula (6-1), the N—$Na_2O$ concentration is a normalized $Na_2O$ surface concentration which is a value obtained by dividing a surface $Na_2O$ concentration by an $Na_2O$ concentration at a depth position of 100 μm, where the $Na_2O$ concentration is a value measured by a fluorescent X-ray analysis using an Na-Kα ray, and the Sn concentration is an Sn deposition amount (unit: as $SnO_2 \mu g/cm^2$) per unit area.

7. The float glass for chemical strengthening according to the above 1, containing a bottom surface coming into contact with a molten metal at the time of forming and a top surface opposing the bottom surface, in which a square (ΔN—$Na_2O)^2$ of a difference ΔN—$Na_2O$ determined by subtracting a normalized $Na_2O$ surface concentration of the bottom surface which is a value obtained by dividing an $Na_2O$ concentration in the bottom surface by an $Na_2O$ concentration at a depth position of 100 μm therefrom, from a normalized $Na_2O$ surface concentration of the top surface which is a value obtained by dividing an $Na_2O$ concentration in the top surface by an $Na_2O$ concentration at a depth position of 100 μm therefrom, is $5.0 \times 10^{-4}$ or less, where each $Na_2O$ concentration is a value measured by a fluorescent X-ray analysis using an Na-Kα ray.

8. The float glass for chemical strengthening according to the above 1, which is used for chemical strengthening in which a chemical strengthening temperature is T (unit: K) and a chemical strengthening time is t (unit: hours) and contains $SiO_2$, in which a dol determined according to the following formula by using respective contents in mass % of $SiO_2$, $Al_2O_3$, MgO, CaO, SrO, BaO, $ZrO_2$, $Na_2O$ and $K_2O$ is 20 or less:

dol=−0.13×$Al_2O_3$−1.88×MgO−2.41×CaO−1.85×SrO−1.35×BaO−1.59×$ZrO_2$+1.50×$Na_2O$+2.42×$K_2O$−129359/T+9.28×$t^{0.5}$+182.88.

$Al_2O_3$, MgO, CaO, SrO, BaO, $ZrO_2$, $Na_2O$ and $K_2O$ are not essential components. A salt used for chemical strengthening typically contains $KNO_3$ in a concentration of from 95 to 100 mass %.

9. The float glass for chemical strengthening according to the above 1, which contains, in mass %, from 60 to 80% of $SiO_2$, from 0 to 8% of $Al_2O_3$, from 8 to 22% of $Na_2O$, from 0 to 7% of $K_2O$, from 0 to 17% of MgO, from 0 to 22% of CaO, from 0 to 8% of SrO, from 0 to 8% of BaO, and from 0 to 5% of $ZrO_2$. Here, for example, containing "from 0 to 7% of $K_2O$" means that $K_2O$ is not essential but it may be contained up to 7%.

Preferable composition range is from 64 to 77% of $SiO_2$, from 0.01 to 7% of $Al_2O_3$, from 10 to 18% of $Na_2O$, from 0 to 5% of $K_2O$, from 1 to 10% of MgO, from 1 to 12% of CaO, from 0 to 5% of SrO, from 0 to 5% of BaO, and from 0 to 3% of $ZrO_2$.

10. The float glass for chemical strengthening according to the above 1, containing, in mass %, from 60 to 80% of $SiO_2$, from 0.01 to 8% of $Al_2O_3$, from 8 to 22% of $Na_2O$, from 0 to 7% of $K_2O$ and from 0 to 5% of $ZrO_2$, in which in the case of containing MgO, CaO, SrO or BaO, the total of the MgO, CaO, SrO and BaO contents is from 5 to 25%, and a ratio $Na_2O/Al_2O_3$ of $Na_2O$ and $Al_2O_3$ contents is 1.5 or more.

11. The float glass for chemical strengthening according to the above 10, in which the $Na_2O/Al_2O_3$ is 6 or less.

12. The float glass for chemical strengthening according to the above 9, containing CaO, SrO or BaO, in which the total of the CaO, SrO and BaO contents is from 1 to 7%.

13. A method for producing a chemically strengthened glass having a depth of compressive stress layer of 20 μm or less, including chemically strengthening the glass for chemical strengthening described in the above 1.

Advantage of the Invention

In the float glass for chemical strengthening of the present invention, the difference in the weathering degrees between the top surface and the bottom surface is small, so that even when the stress produced by chemical strengthening is not decreased or a polishing treatment, etc. before chemical strengthening is simplified or omitted, the warpage of the float glass after chemical strengthening can be reduced and an excellent flatness can be obtained.

BRIEF DESCRIPTION OF THE DRAWINGS

FIG. 4 is a schematic view illustrating the method for calculating the ion exchange amount in fluorescent X-ray analysis.

FIG. 5A is a graph showing an amount of K$_2$O in a raw sheet. FIG. 5B is a graph showing an amount of K$_2$O in a chemical strengthened article. FIG. 5C is a graph showing the ion exchange amount. FIG. 5D illustrates how the ion exchange amount is calculated.

FIG. 6 is a graph plotting, on the abscissa, the difference $\Delta(N—Na_2O^2)$ (Top-Bottom) between squared normalized Na$_2$O surface concentrations in top surface and bottom surface of glass to be subjected to chemical strengthening, and on the ordinate, Δwarpage amount.

FIG. 10 is a longitudinal cross-sectional view of the apparatus for producing the float glass for chemical strengthening of the present invention.

FIG. 11 is a cross-sectional view of a flat panel display in which the float glass for chemical strengthening of the present invention is chemically strengthened and then used as a cover glass for a flat panel display.

MODE FOR CARRYING OUT THE INVENTION

1. Weathering of Glass

The H profile ($^1$H$^-$/$^{30}$Si$^-$) on the surface of a soda-lime glass produced by a float method was analyzed by a secondary ion mass spectrometry apparatus (SIMS), and as a result, the depth of weathered (hydrated and dealkalized) layer was about 3 μm. This implies that at the time of chemical strengthening to an ion-exchange depth of 20 μm or less, as a cause of warpage occurring due to the difference in the chemical strengthening behaviors between the bottom surface and the top surface, the difference between weathering degrees in the top surface and the bottom surface is important.

The "weathering" as used in the present invention indicates a phenomenon where the glass surface is degraded due to corrosion of the glass surface by the atmosphere, usually, by the effect of humidity, and in the present invention, this indicates a phenomenon where an alkali metal component, typically, Na$_2$O, in the surface layer of glass is desorbed. The weathering degree of glass can be analyzed by measuring the Na$_2$O concentration by fluorescent X-ray analysis.

Figure 1:
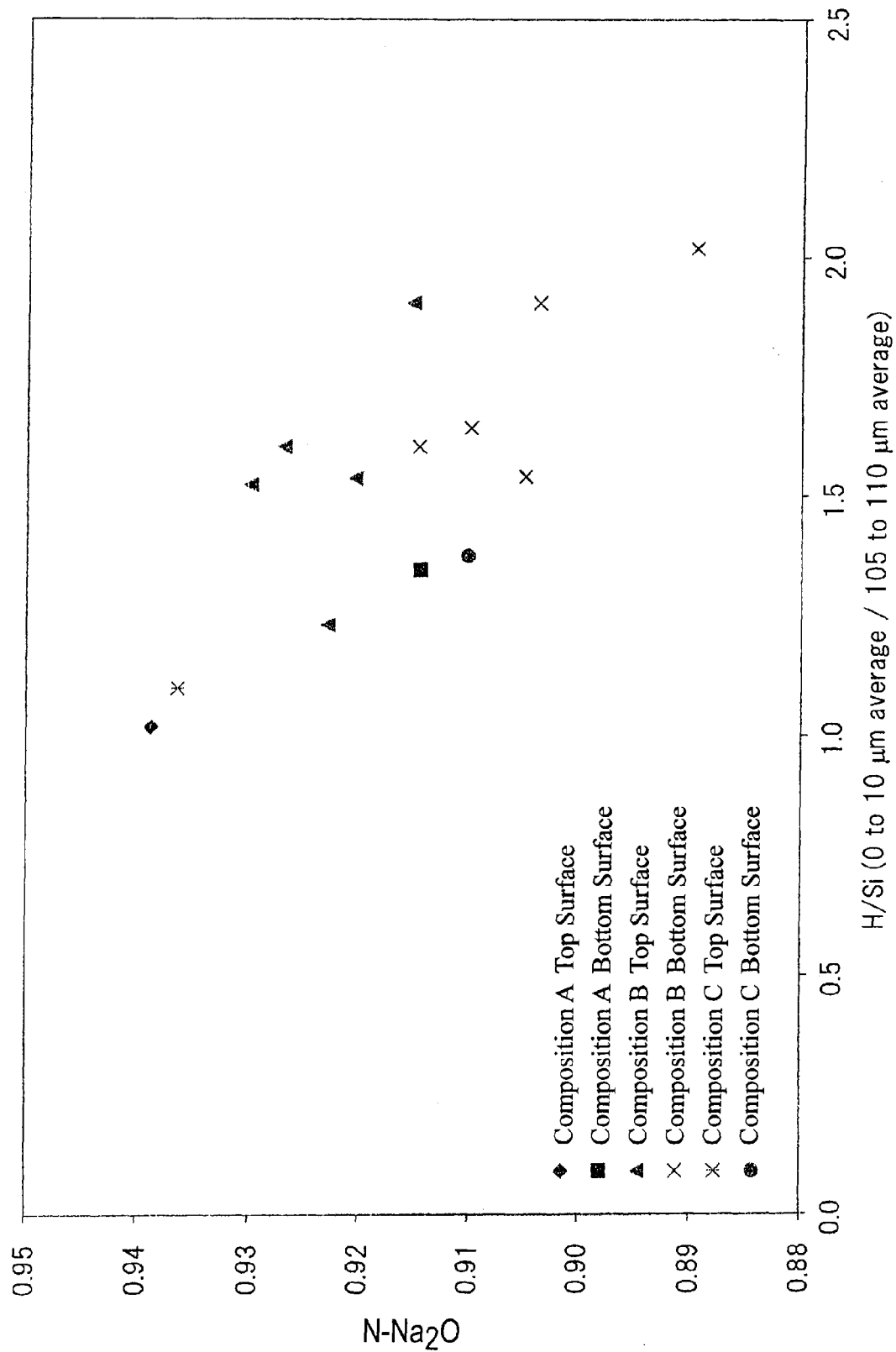
FIG. 1 is a view showing the correlation between the normalized hydrogen concentration [obtained by dividing the average H/Si at (H/Si) 0 to 10 μm in SIMS analysis by the average H/Si at 105 to 110 μm] and the normalized $Na_2O$ surface concentration (obtained by dividing the surface Na$_2$O concentration in fluorescent X-ray analysis by the Na$_2$O concentration at a depth position of 100 μm) in the surface layer of a soda-lime glass sheet (raw sheet) before chemical strengthening.

FIG. 1 illustrates the correlation between the normalized hydrogen concentration (SIMS analysis) and the normalized Na$_2$O surface concentration (obtained by dividing the surface Na$_2$O concentration in fluorescent X-ray analysis by the Na$_2$O concentration at a depth position of 100 μm) in the surface layer of a soda-lime glass sheet (raw sheet) before chemical strengthening. As shown in FIG. 1, in the surface layer of a soda-lime glass sheet before chemical strengthening, the normalized hydrogen concentration is in an inverse relationship with the normalized Na$_2$O surface concentration.

Figure 2:
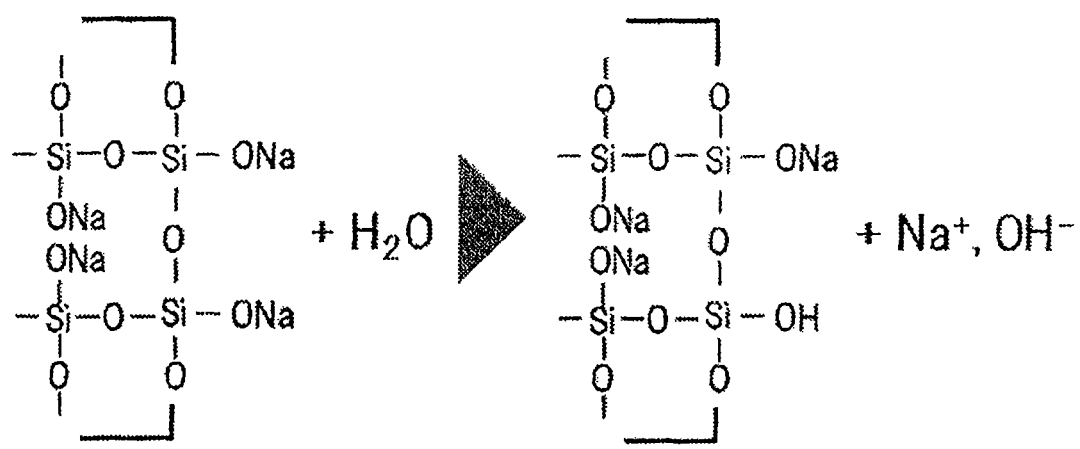
FIG. 2 illustrates the mechanism in a glass before chemical strengthening, where Na$^+$ in glass is ion-exchanged with H$^+$ in the atmosphere.

The graph of FIG. 1 indicates that as explained in FIG. 2, in the glass before chemical strengthening, Si—O—Na constituting the glass reacts with H$_2$O in the atmosphere and Na$^+$ and H$^+$ are ion-exchanged. Accordingly, the normalized hydrogen concentration in the glass surface layer is considered to increase as the weathering degree of glass is larger.

Figure 3:
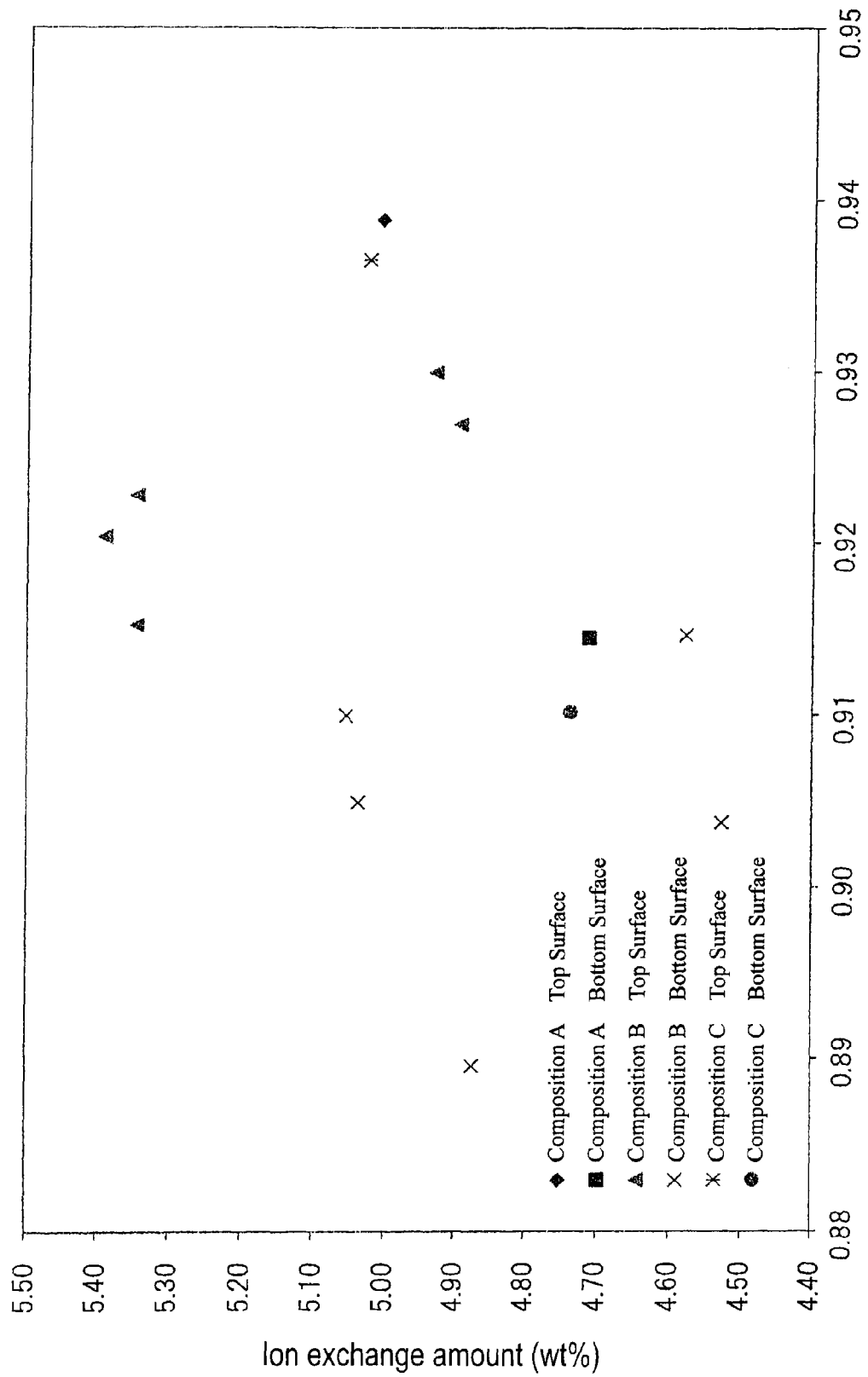
FIG. 3 is a view showing the correlation between the ion exchange amount (K$_2$O, wt %) (fluorescent X-ray analysis) of a soda-lime glass sheet after chemical strengthening and the normalized Na$_2$O surface concentration (obtained by dividing the surface Na$_2$O concentration in fluorescent X-ray analysis by the Na$_2$O concentration at a depth position of 100 μm) before chemical strengthening (raw sheet); where wt % is mass %.
Figure 5A:
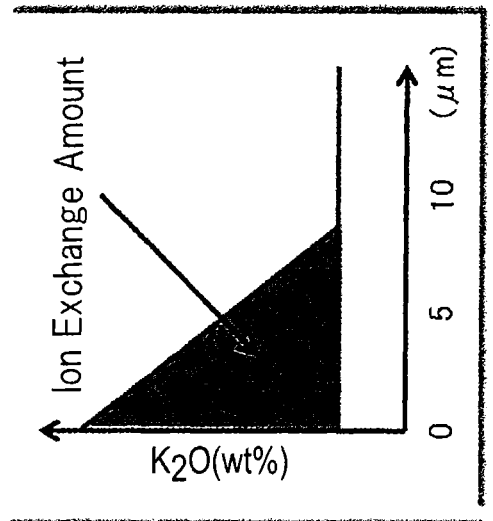
FIGS. 5A, 5B, 5C and 5D are schematic views illustrating the mechanism where when a soda-lime glass sheet in which Na$^+$ and H$^+$ are ion-exchanged is chemically strengthened by dipping it in a KNO$_3$ molten salt, the ion exchange amount decreases.
Figure 5B:
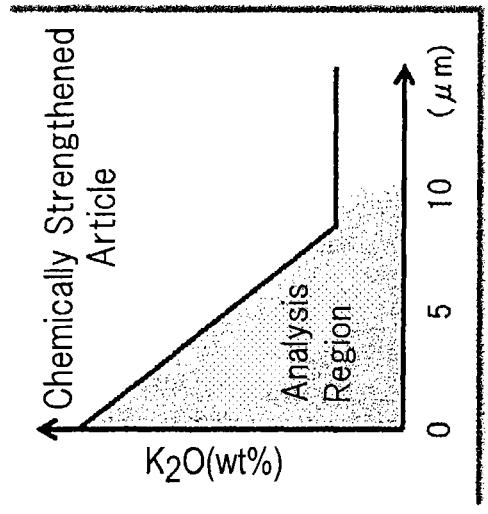
Figure 5C:
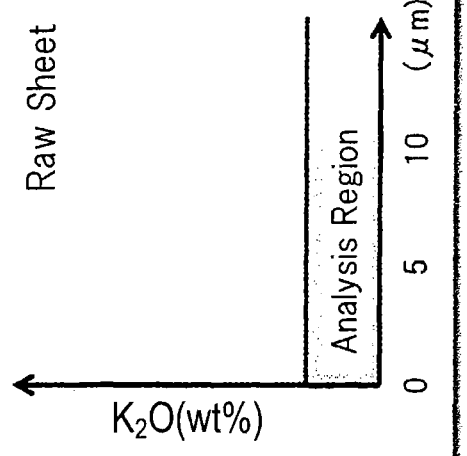
Figure 5D:
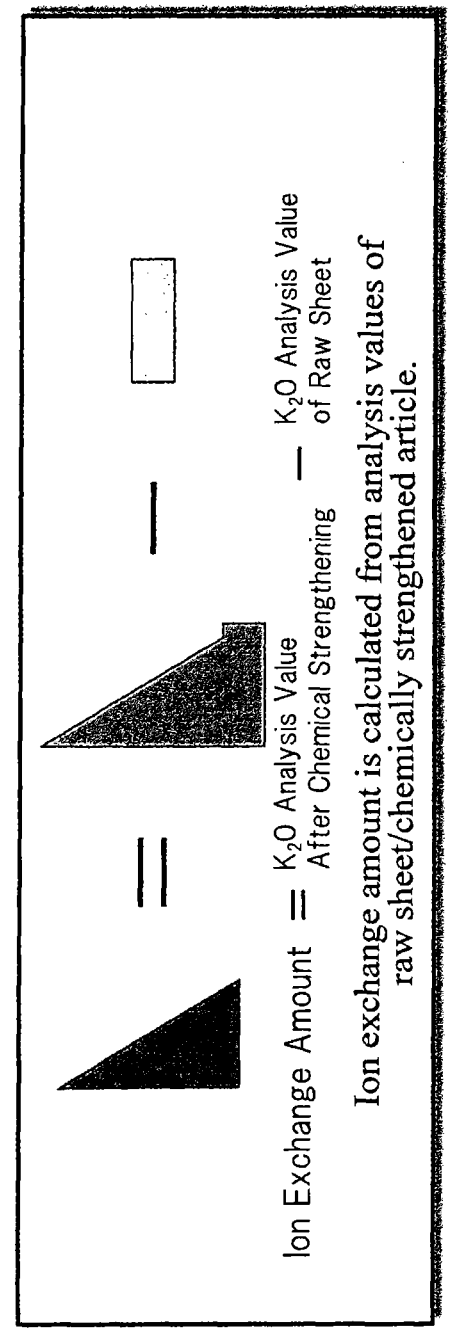

FIG. 3 illustrates the correlation between the ion exchange amount (wt %) (fluorescent X-ray analysis) of a soda-lime glass sheet after chemical strengthening and the normalized Na$_2$O surface concentration of a raw sheet. Here, with regard to the ion exchange amount, as shown in FIG. 4, the value obtained by subtracting the K$_2$O analysis value before chemical strengthening (raw sheet) from the K$_2$O analysis value after chemical strengthening is defined as the ion exchange amount.

It is seen from the graph of FIG. 3 that as the Na$_2$O concentration in glass before chemical strengthening is higher, namely, as the weathering degree of glass is smaller, the ion exchange amount after chemical strengthening increases.

The graph of FIG. 3 also implies the following. That is, as shown in FIGS. 5A, 5B, 5C and 5D, when a soda-lime glass sheet in which Na$^+$ and H$^+$ are ion-exchanged as shown in FIG. 2 is chemically strengthened by dipping it in a KNO$_3$ molten salt, the ion exchange of Na$^+$ in glass with K$^+$ is governed by entropy but in the case of exchange of H$^+$ with K$^+$, the ion exchange is considered to be not driven enthalpically, because H in glass is present as SiOH (weak acid) and if H+ and K+ are ion-exchanged, HNO$_3$ (strong acid) is produced.

Accordingly, it is thought that the weathering degree of a soda-lime glass before chemical strengthening affects the ion exchange amount and the difference in the ion exchange amount between the top surface and the bottom surface causes the generation of warpage after chemical strengthening. This leads to an understanding that in order to suppress warpage of a soda-lime glass after chemical strengthening, it is important to control the difference (the Na$_2$O concentration difference between the top surface and the bottom surface) in the weathering degrees of the glass surface layer between top surface and bottom surface of glass before chemical strengthening.

2. Sn Concentration

The Sn (tin) profile ($^{120}$Sn$^-$/$^{30}$Si$^-$) in the bottom surface of a soda-lime glass produced by a float method was analyzed by a secondary ion mass spectrometry apparatus (SIMS), and as a result, the depth of ion-exchanged layer and the Sn invasion depth were about 7 µm. This implies that at the time of chemical strengthening of low DOL to an ion-exchange depth, i.e., DOL, of 20 µm or less, as a cause of warpage occurring due to the difference in the chemical strengthening behaviors between the bottom surface and the top surface, the Sn concentration needs to be taken into account.

In this connection, both $\Delta$(N—Na$_2$O$^2$) and ($\Delta$N—Na$_2$O)$^2$ depend on the difference of weathering degrees but are not dependent directly on the Sn concentration. However, invasion of Sn into the bottom surface in a float bath is considered to occur due to ion-exchange with Na of the glass surface layer. Therefore, in glass having a large Sn deposition amount, the Na concentration of the surface layer is assumed to be low. Accordingly, the normalized Na$_2$O surface concentration has a relationship with the Sn concentration. In other words, although not explicit, both $\Delta$(N—Na$_2$O$^2$) and ($\Delta$N—Na$_2$O)$^2$ can be said to depend on the Sn concentration.

At the time of float forming, when glass is densified by the invasion of Sn into the glass, the pathway for ion-exchange of Na ion with K ion is narrowed and, as a result, the ion exchange reaction is disturbed and the chemical strengthening is inhibited in the Sn invaded surface (bottom surface). This is considered to cause difference in the chemical strengthening behaviors between the top surface and the bottom surface, leading to warpage of the glass.

The Sn concentration of glass can be determined by measuring the Sn deposition amount per unit area. Specifically, it can be determined, for example, by etching the glass with a hydrofluoric acid solution and quantitatively determining the Sn concentration in the solution by ICP emission spectrometry.

3. Hydrogen Concentration

The float glass for chemical strengthening of the present invention is formed by a float method and has a bottom surface coming into contact with a molten metal at the time of forming and a top surface opposing the bottom surface. As described below, the hydrogen concentration difference between the top surface and the bottom surface is considered to sometimes work out to one of causes of warpage that is caused by chemical strengthening of the float glass.

In the production of glass by a float method, a glass plate is produced by continuously feeding onto a surface of a molten metal retained in a float bath, a molten glass from an upstream side to form a glass ribbon, concurrently drawing the formed glass ribbon from a downstream side end of the float bath, and annealing it in a lehr.

In the production of glass by a float method, an apparatus usually used in a type where a glass tank furnace and a float bath are connected through a canal and a spout and the flow passage is narrowed down. In this case, since the glass must be spread in the float bath, a molten glass at a higher temperature than in the case of another type of apparatus described later is poured onto the molten metal surface and formed.

At this time, when the hydrogen concentration in glass is high, hydrogen enters as the form of SiOH into the Si—O—Si bond network of glass, and the Si—O—Si bond is broken. When the hydrogen concentration in glass is high, the Si—O—Si bond is broken in many portions and since this leads to deterioration of thermal characteristics such as glass transition temperature, stress relaxation occurs at the time of chemical strengthening in which the glass is heated at a high temperature, resulting in decrease of the stress.

For this reason, the degree of stress produced at the time of chemical strengthening is low in a glass surface having a higher hydrogen concentration, out of the top surface and bottom surface in a float glass, and a stress is likely to be produced at the time of chemical strengthening in a glass surface having a lower hydrogen concentration.

In other words, it is considered that when a float glass having a lower hydrogen concentration in the top surface than in the bottom surface is chemically strengthened, a higher stress is produced in the top surface having a low hydrogen concentration than in the bottom surface having a high hydrogen concentration, and the glass is warped to project toward the top surface side, resulting in occurrence of warpage.

Therefore, as the hydrogen concentration in the top surface of a float glass is closer to that in the bottom surface, i.e., as the absolute value of the hydrogen concentration difference between the top surface and the bottom surface is smaller, the degree of stress produced comes close to an equilibrium state between the top surface and the bottom surface after chemical strengthening, and therefore the warpage is decreased.

In the present invention, since the average hydrogen concentration itself and the average hydrogen concentration difference itself can hardly be measured with good precision, the [$^1$H$^-$/$^{30}$Si$^-$] (also referred to as H/Si) proportional to the average hydrogen concentration is used as a direct indicator of the average hydrogen concentration, and the "difference in the normalized hydrogen concentrations between the top surface and the bottom surface" and the "difference in the normalized intensities between the top surface and the bottom surface", which are proportional to the average hydrogen concentration difference above, are used as a direct indicator of the average hydrogen concentration difference.

In the present specification, the [$^1$H$^-$/$^{30}$Si$^-$] is a value measured under the following analysis conditions.

(Analysis Conditions)

Measurement apparatus: secondary ion mass spectrometry apparatus with a quadrupole mass spectrometer Primary ion species: Cs$^+$ Primary accelerating voltage: 5.0 kV Primary ion current: 1 µA Primary ion incident angle (angle from direction perpendicular to sample surface): 60°

Luster size: 200×200 µm$^2$

Detection region: 40×40 µm$^2$

Secondary ion polarity: minus

Electron gun for neutralization: used

The [$^1$H$^-$/$^{30}$Si$^-$], normalized intensity and normalized hydrogen concentration are described below. The secondary ion intensity $I_{M1}$ of isotope $M_1$ of element M in secondary ion mass spectrometry is proportional to the primary ion intensity $I_P$, sputter ratio Y of matrix, concentration $C_M$ (ratio to the total concentration) of element M, existence probability $\alpha_1$ of isotope $M_1$, secondary ionization ratio $\beta_M$ of element M, and transmission efficiency $\eta$ (including detection efficiency of detector) of mass spectrometer.

$$I_{M1}=A\cdot I_P\cdot Y\cdot C_M\cdot \alpha_1\cdot \beta_M\cdot \eta \qquad \text{(formula 1)}$$

In the formula, A is the ratio of detection area of secondary ion to scanning range of primary ion beam. In general, $\eta$ of an apparatus can be hardly determined and in turn, the absolute value of $\beta_M$ cannot be obtained. Therefore, $\eta$ is eliminated by using the main component element or the like in the same sample as a reference element and employing the ratio to (formula 1).

Assuming that the reference element is R and its isotope is $R_j$, (formula 2) is established:

$$I_{M1}/I_{Rj}=(C_M\cdot\alpha_1\cdot\beta_M)/(C_R\cdot\alpha_j\cdot\beta_R)=C_M/K \qquad \text{(formula 2)}$$

in which K is a relative sensitivity factor of element M to element R.

$$K=(C_R\cdot\alpha_j\cdot\beta_R)/(\alpha_1\cdot\beta_M) \qquad \text{(formula 3)}$$

In this case, the concentration of element M is determined according to (formula 4):

$$C_M=K\cdot I_{M1}/I_{Rj} \qquad \text{(formula 4)}$$

In the present invention, $^1$H$^-$ and $^{30}$Si$^-$ correspond to $M_1$ and $R_j$, respectively. Therefore, from the (formula 2), the intensity ratio [$^1$H$^-$/$^{30}$Si$^-$] of those two is equivalent to a value obtained by dividing the average hydrogen concentration $C_H$ by K. That is, the [$^1$H$^-$/$^{30}$Si$^-$] is a direct indicator of the average hydrogen concentration.

The normalized intensity is a value obtained by dividing [$^1$H$^-$/$^{30}$Si$^-$] at a certain depth x by [$^1$H$^-$/$^{30}$Si$^-$] at a depth of 105 to 110 μm, that is, a value obtained by dividing $C_H$/K at a certain depth x by $C_H$/K at a depth of 105 to 110 μm. Since K is eliminated, the normalized intensity is eventually the same as a value obtained by dividing $C_H$ at a depth x by $C_H$ at a depth of 105 to 110 μm and, namely, is the normalized hydrogen concentration at a depth x.

The reason why the average hydrogen concentration at a depth of 105 to 110 μm is employed as the basis when calculating the normalized hydrogen concentration is because the region at a depth of 105 to 110 μm is considered to be an inner region where the average hydrogen concentration does not vary.

The absolute value of the normalized intensity difference between the top surface and the bottom surface in a float glass is obtained by secondary ion mass spectrometry (SIMS analysis), for example, through the following procedures (i) to (iii). Here, the analysis conditions described below are for exemplification and should be appropriately changed according to the measurement apparatus, sample, etc.

(i) In each of the top surface and the bottom surface, the secondary ion mass spectrometry is performed to a depth of 20 μm from the surface layer under the following analysis conditions.

(Analysis Conditions)

Measurement apparatus: secondary ion mass spectrometry apparatus with a quadrupole mass spectrometer Primary ion species: Cs$^+$ Primary accelerating voltage: 5.0 kV Primary ion current: 1 μA Primary ion incident angle (angle from direction perpendicular to sample surface): 60°

Luster size: 200×200 μm$^2$

Detection region: 40×40 μm$^2$

Secondary ion polarity: minus

Electron gun for neutralization: used

In the case where the intensity of $^{30}$Si$^-$ at a depth of 55 μm is smaller than the intensity of $^{30}$Si$^-$ at a depth of 5 μm by more than 3%, the analysis is preferably performed on a sample in which the surface of a glass substrate is previously etched by about 45 μm.

More specific analysis conditions are, for example, as follows.

(Analysis Conditions)

Measurement apparatus: secondary ion mass spectrometry apparatus with a quadrupole mass spectrometer Primary ion species: Cs$^+$ Primary accelerating voltage: 5.0 kV Primary ion current: 1 μA Primary ion incident angle (angle from direction perpendicular to sample surface): 60°

Luster size: 200×200 μm$^2$

Detection region: 40×40 μm$^2$

Sputter rate: 14 nm/sec

Secondary ion polarity: minus

Electron gun for neutralization: used

The secondary ion mass spectrometry apparatus with a quadrupole mass spectrometer includes, for example, ADEPT 1010, manufactured by Ulvac-Phi, Inc.

(ii) A value obtained by dividing [$^1$H$^-$/$^{30}$Si$^-$] at a depth of 0 to 10 μm in the [$^1$H$^-$/$^{30}$Si$^-$] profile obtained by secondary ion mass spectrometry by [$^1$H$^-$/$^{30}$Si$^-$] at a depth of 105 to 110 μm is defined as the normalized intensity at a depth of 0 to 10 μm in secondary ion mass spectrometry.

(iii) With regard to the normalized intensity at a depth of 0 to 10 μm obtained by secondary ion mass spectrometry, the absolute value of the difference between the top surface and the bottom surface is calculated.

4. Ion Exchange Amount

The ion exchange amount is a stress generation factor and is in a proportional relationship with the K$_2$O concentration in glass after chemical strengthening. Therefore, the difference between ion exchange amounts in the top surface and the bottom surface can be analyzed by the K$_2$O concentration difference. The K$_2$O concentration can be analyzed by fluorescent X-ray analysis.

5. Warpage Amount

The float glass for chemical strengthening of the present invention is a float glass having a small amount of warpage after chemical strengthening. The warpage amount of the float glass can be measured by a contact-type surface profile analyzer [for example, SURFCOM (trade name), manufactured by Tokyo Seimitsu Co., Ltd.].

The warpage amount is measured as the difference between the highest point and the lowest point when measured with a contact-type surface profile analyzer, after correcting the base line so that the measurement start point and the measurement end point can be aligned at the same level. The warpage amount is indicated by a positive value when the float glass is warped in the convex direction to the top surface, and by a negative value when warped in the convex direction to the bottom surface.

The change in the warpage amount of the float glass before and after chemical strengthening can be measured according to the following formula.

ΔWarpage amount=(warpage amount after chemical strengthening)−(warpage amount before chemical strengthening)  (formula)

In the present invention, the measurement is performed on a central 9 cm-square region of a 10 cm-square float glass, and the absolute value of Δwarpage amount in terms of sheet thickness of 07 mm is preferably 58 μm or less, 56 μm or less, 54 μm or less, or 52 μm or less. When the absolute value of Δwarpage amount is not more than the upper limit above, the warpage after chemical strengthening can be decreased.

The CS (surface compressive stress) and DOL (depth of compressive stress layer) can be measured by a surface stress meter. In regard to the float glass for chemical strengthening of the present invention, the surface compressive stress of the chemically strengthened glass is preferably 650 MPa or more, and it is preferably used when the depth of compressive stress layer is 20 μm or less. When the depth of compressive stress layer is 20 μm or less, the product after chemical strengthening can be cut, and this is preferred. In this viewpoint, the depth of compressive stress layer is more preferably 15 μm or less.

6. Parameters

The discussion above implies the following parameters.

(1) $Na_2O$ Concentration Difference Between Top Surface and Bottom Surface Before Chemical Strengthening, and ΔWarpage Amount It is considered that for controlling the warpage after chemical strengthening of a soda-lime glass, it is important to control the weathering degree, hydrogen concentration and Sn concentration in the glass surface layer before chemical strengthening.

Here, as shown in FIG. 1, in the surface layer in glass before chemical strengthening, the normalized hydrogen concentration is in an inverse relationship with the normalized $Na_2O$ surface concentration. In addition, as shown in FIG. 3, as the normalized $Na_2O$ surface concentration in glass before chemical strengthening is higher, the ion exchange amount after chemical strengthening is increased, and thus, the normalized $Na_2O$ surface concentration in glass before chemical strengthening is in a proportional relationship with the ion exchange amount.

Furthermore, when the increase in the hydrogen concentration of the glass surface layer is large, the Si—O—Si bond is broken in many portions and since this leads to deterioration of thermal characteristics such as glass transition temperature, stress relaxation occurs at the time of chemical strengthening in which the glass is heated at a high temperature, resulting in decrease of the stress. Therefore, it can be considered that stress generation resulting from chemical strengthening is attributable to the ion exchange amount and the relaxation degree. For this reason, the normalized $Na_2O$ surface concentration difference between top surface and bottom surface in glass before chemical strengthening is considered to have a correlation with the Δwarpage amount.

(1A) Difference Between Squared Normalized $Na_2O$ Surface Concentrations in Top Surface and Bottom Surface, and ΔWarpage Amount FIG. 6 shows a graph plotting, on the abscissa, the difference $\Delta(N-Na_2O^2)$ (Top-Bottom) obtained by subtracting the squared normalized $Na_2O$ surface concentration of the bottom surface from the squared normalized $Na_2O$ surface concentration of the top surface, and on the ordinate, Δwarpage amount.

It is seen from the graph shown in FIG. 6 that the difference $\Delta(N-Na_2O^2)$ between squared normalized $Na_2O$ surface concentrations in the top surface and the bottom surface of a soda-lime glass sheet before chemical strengthening and the Δwarpage amount have a correlation represented by the following formula (1-1).

ΔWarpage amount=370×Δ(N—$Na_2O^2$)+45   formula (1-1)

In formula (1-1), the $\Delta(N-Na_2O^2)$ is the difference between squares of the values obtained by measuring, by fluorescent X-ray analysis, the normalized $Na_2O$ surface concentrations in the top surface and the bottom surface of glass to be subjected to chemical strengthening and is determined according to the following formula (1-2).

Δ(N—$Na_2O^2$)=(normalized $Na_2O$ surface concentration in top surface before chemical strengthening)$^2$−(normalized $Na_2O$ surface concentration in bottom surface before chemical strengthening)$^2$   formula (1-2)

Here, the normalized $Na_2O$ surface concentration is a value obtained by dividing the surface $Na_2O$ concentration by the $Na_2O$ concentration at a depth position of 100 μm. Each $Na_2O$ concentration is a value calculated from the relative intensity ratio to a standard sample by measuring the intensity of Na-Kα ray by fluorescent X-ray analysis. Incidentally, the $Na_2O$ concentration at a depth position of 100 μm is an $Na_2O$ concentration obtained by measuring the surface with a fluorescent X-ray after grinding off the glass to a depth of 100 μm from the surface. In addition, the analysis depth of the value measured by fluorescent X-ray analysis using an Na-Kα ray is typically 3 μm.

The difference between squared normalized $Na_2O$ surface concentrations in the top surface and the bottom surface of glass to be subjected to chemical strengthening is 0.040 or less, preferably 0.035 or less, 0.030 or less, or 0.025 or less. When the difference between squared normalized $Na_2O$ surface concentrations in the top surface and the bottom surface of glass to be subjected to chemical strengthening is 0.040 or less, even if a polishing treatment, etc. before chemical strengthening is simplified or omitted, warpage of the float glass after chemical strengthening can be reduced and excellent flatness can be obtained.

Figure 16:
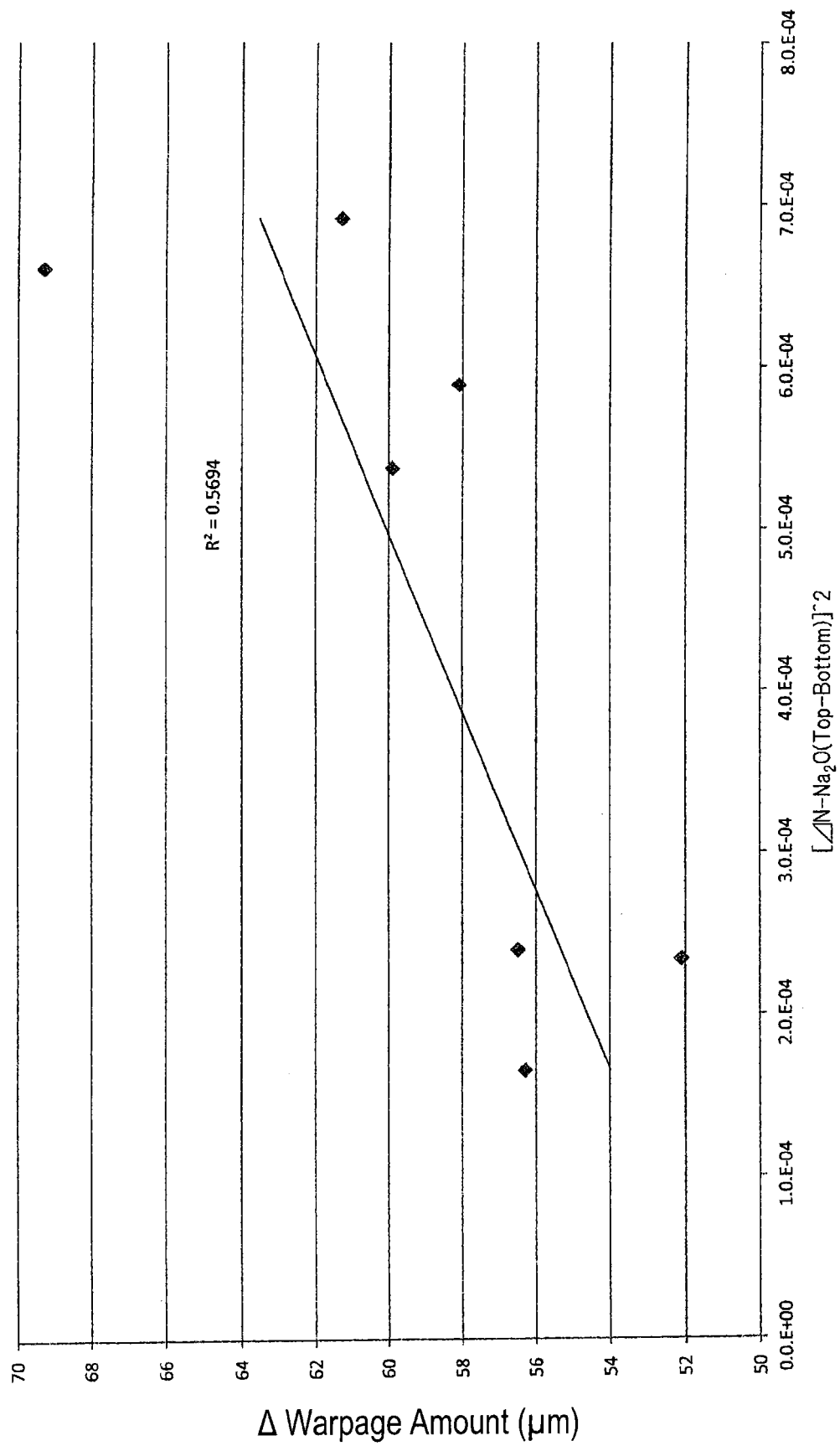
FIG. 16 shows a graph plotting, on the abscissa, a square $[\Delta N—Na_2O \text{ (Top-Bottom)}]^2$ of the difference obtained by subtracting the normalized Na$_2$O surface concentration of the bottom surface from the normalized Na$_2$O surface concentration of the top surface, and on the ordinate, Δwarpage amount.

(1B) Square of Difference Between Normalized $Na_2O$ Surface Concentrations in Top Surface and Bottom Surface, and ΔWarpage Amount FIG. 16 shows a graph plotting, on the abscissa, a square $[\Delta N-Na_2O \text{ (Top-Bottom)}]^2$ of the difference determined by subtracting the normalized $Na_2O$ surface concentration of the bottom surface which is a value obtained by dividing the $Na_2O$ concentration in bottom surface by the $Na_2O$ concentration at a depth position of 100 μm, from the normalized $Na_2O$ surface concentration of the top surface which is a value obtained by dividing the $Na_2O$ concentration in the top surface by the $Na_2O$ concentration at a depth position of 100 μm, and on the ordinate, Δwarpage amount.

It is seen from the graph shown in FIG. 16 that the square $[\Delta N-Na_2O \text{ (Top-Bottom)}]^2$ of the difference determined by subtracting the normalized $Na_2O$ surface concentration of the bottom surface from the normalized $Na_2O$ surface concentration of the top surface and the Δwarpage amount have a correlation represented by the following formula (7-1).

ΔWarpage amount=18000×(ΔN—$Na_2O$)$^2$+51   formula (7-1)

In formula (7-1), the $(\Delta N\text{---}Na_2O)^2$ is a square of the difference between the values obtained by measuring, by fluorescent X-ray analysis, the normalized $Na_2O$ surface concentrations in the top surface and the bottom surface of glass to be subjected to chemical strengthening and is determined according to the following formula (7-2).

$(\Delta N\text{---}Na_2O)^2 = [(\text{normalized } Na_2O \text{ surface concentration in top surface before chemical strengthening}) - (\text{normalized } Na_2O \text{ surface concentration in bottom surface before chemical strengthening})]^2$ formula (7-2)

The square of the difference between normalized $Na_2O$ surface concentrations in the top surface and the bottom surface of glass to be subjected to chemical strengthening is $5.0 \times 10^{-4}$ or less, preferably $4.5 \times 10^{-4}$ or less, $4.0 \times 10^{-4}$ or less, or $3.5 \times 10^{-4}$ or less. When the square of the difference between normalized $Na_2O$ surface concentrations in the top surface and the bottom surface of glass to be subjected to chemical strengthening is $5.0 \times 10^{-4}$ or less, even if a polishing treatment, etc. before chemical strengthening is simplified or omitted, warpage of the float glass after chemical strengthening can be reduced and excellent flatness can be obtained.

The $Na_2O$ concentration is adjusted by the method described later in (A) of "7. Production Method of Glass", whereby the normalized $Na_2O$ surface concentrations in the top surface and the bottom surface of glass to be subjected to chemical strengthening can be adjusted, and $\Delta(N\text{---}Na_2O^2)$ or $(\Delta N\text{---}Na_2O)^2$ can be adjusted. Specifically, it is preferable, for example, to decrease the $Na_2O$ concentration in the top surface by spraying water vapor or $SO_2$ gas onto the top surface at the time of annealing the glass or increase the $Na_2O$ concentration in the bottom surface by lowering the flow rate of $SO_2$ gas sprayed onto the bottom surface for the purpose of scratch prevention.

(2) Ion Exchange Amount Difference Between Top Surface and Bottom Surface after Chemical Strengthening and $\Delta$Warpage Amount The $\Delta$ion exchange amount 1 that is the difference between ion exchange amounts in the top surface and the bottom surface after chemical strengthening is considered to have a correlation with the $\Delta$warpage amount.

The ion exchange amount is proportional to the $Na_2O$ concentration before chemical strengthening and inhibited by Sn and therefore, can be determined according to the following formula (2-1).

Ion exchange amount 1=5.51×(normalized $Na_2O$ surface concentration)−0.038×(Sn concentration) formula (2-1)

Hereinafter, the term "ion exchange amount" is sometimes used for indicating the ion exchange amount 1.

In formula (2-1), the normalized $Na_2O$ surface concentration is a value obtained by dividing the surface $Na_2O$ concentration by the $Na_2O$ concentration at a depth position of 100 μm. Here, each $Na_2O$ concentration is a value measured by fluorescent X-ray analysis using an Na-Kα ray. In addition, the Sn concentration is an Sn deposition amount (unit: as $SnO_2 \mu g/cm^2$) per unit area of the top surface and the bottom surface.

The difference between ion exchange amounts 1 in the top surface and the bottom surface can be determined according to the following formula (2-2).

Ion exchange amount 1 difference=(ion exchange amount 1 in top surface)−(ion exchange amount 1 in bottom surface) formula (2-2)

Figure 7:
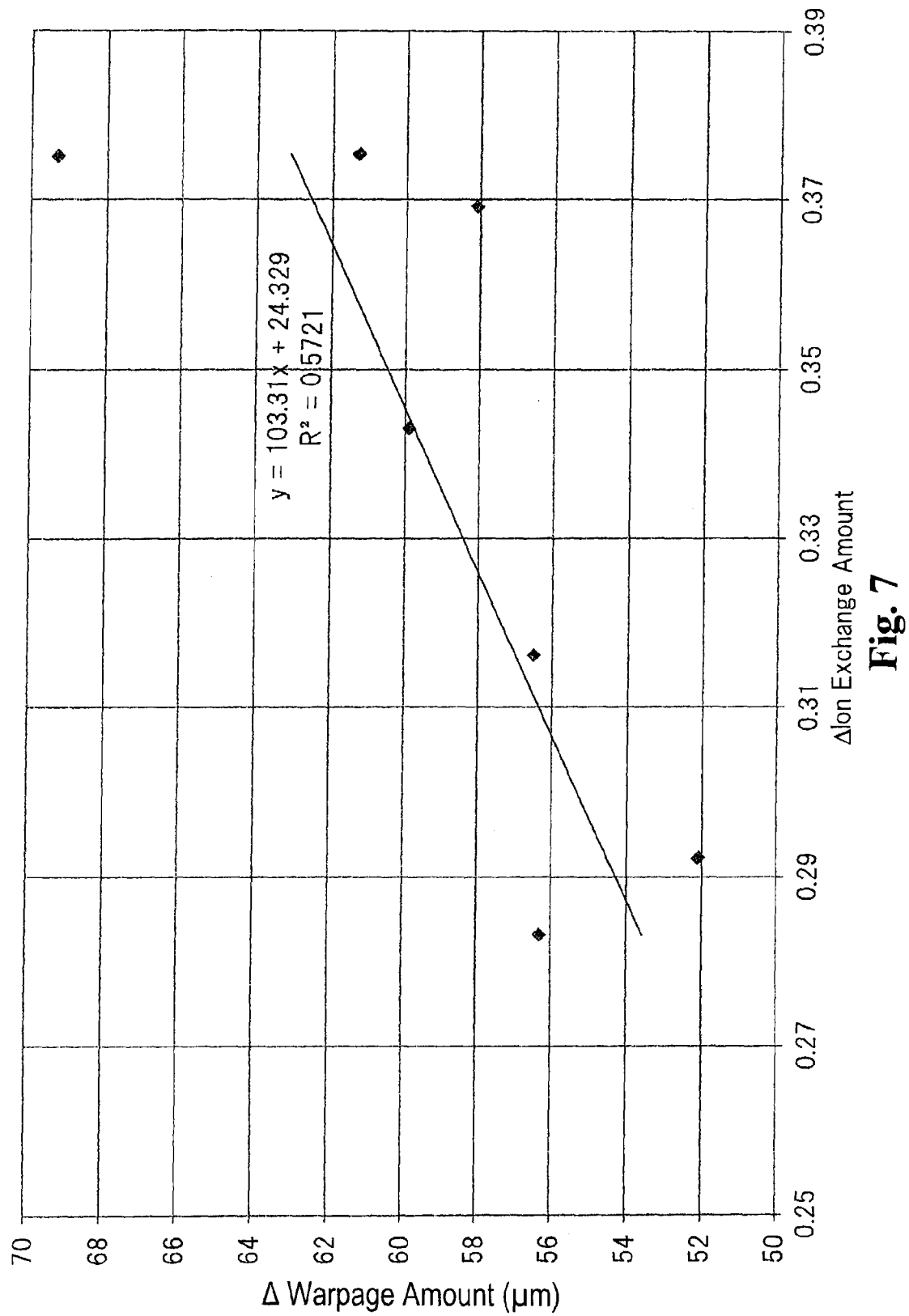
FIG. 7 is a graph plotting, on the abscissa, the difference between ion exchange amounts in top surface and bottom surface, and on the ordinate, Δwarpage amount.

FIG. 7 shows a graph plotting, on the abscissa, $\Delta$ion exchange amount 1 that is the difference between ion exchange amounts in the top surface and the bottom surface, and on the ordinate, $\Delta$warpage amount. It is seen from the graph shown in FIG. 7, the $\Delta$ion exchange amount 1 and the $\Delta$warpage amount have a correlation represented by the following formula (2-3).

$\Delta$Warpage amount=103×($\Delta$ion exchange amount 1)+24 formula (2-3)

The $\Delta$ion exchange amount 1 is 0.32 or less, preferably 0.30 or less, 0.28 or less, 0.26 or less, or 0.24 or less.

When the difference between ion exchange amounts 1 in the top surface and the bottom surface after chemical strengthening, determined according to formulae (2-1) and (2-2), is 0.32 or less, even if a polishing treatment, etc. before chemical strengthening is simplified or omitted, warpage of the float glass after chemical strengthening can be reduced and excellent flatness can be obtained.

The $Na_2O$ concentration and the Sn concentration in the bottom surface are adjusted by the method described later in (A) of "7. Production Method of Glass", whereby the $\Delta$ion exchange amount 1 that is the difference between ion exchange amounts 1 in the top surface and the bottom surface after chemical strengthening can be adjusted. Specifically, it is preferable, for example, to decrease the $Na_2O$ concentration in the top surface by spraying water vapor or $SO_2$ gas onto the top surface at the time of annealing the glass, increase the $Na_2O$ concentration in the bottom surface by lowering the flow rate of $SO_2$ gas sprayed onto the bottom surface for the purpose of scratch prevention, or decrease the invasion amount of Sn into the bottom surface by lowering the temperature upstream of the float bath or increasing the hydrogen concentration in the atmosphere.

(3) Correlation of Hydrogen Concentration Difference and Sn Concentration Difference Between Top Surface and Bottom Surface Before Chemical Strengthening and Ion Exchange Amount Difference with $\Delta$Warpage Amount When multiple regression analysis is performed using, as factors, the hydrogen concentration difference, Sn concentration difference and ion exchange amount difference between the top surface and the bottom surface before chemical strengthening, and the $\Delta$warpage amount, the following formula (3-1) is obtained.

W1=−16×($\Delta$H/Si)−6.47×(Sn concentration difference)−43.8×($\Delta$ion exchange amount 1) formula (3-1)

In formula (3-1), the $\Delta$H/Si is the difference (difference between normalized hydrogen concentrations) between values obtained by measuring, by SIMS analysis, the hydrogen concentration difference between the top surface and the bottom surface before chemical strengthening and is determined according to the following formula (3-2).

$\Delta$H/Si=(normalized hydrogen concentration in top surface before chemical strengthening)−(normalized hydrogen concentration in bottom surface before chemical strengthening) formula (3-2)

In formula (3-1), the Sn concentration difference is the difference obtained by subtracting the Sn deposition amount (unit: as $SnO_2 \mu g/cm^2$) per unit area of the top surface from the Sn deposition amount (unit: as $SnO_2 \mu g/cm^2$) per unit area of the bottom surface, and in the case where the glass does not contain $SnO_2$, this is equivalent to the Sn deposition amount per unit area of the bottom surface.

The $\Delta$ion exchange amount 1 is a value obtained by subtracting the ion exchange amount in the bottom surface from the ion exchange amount 1 in the top surface. The ion exchange amount is determined according to the above-mentioned formula (2-1).

Figure 12:
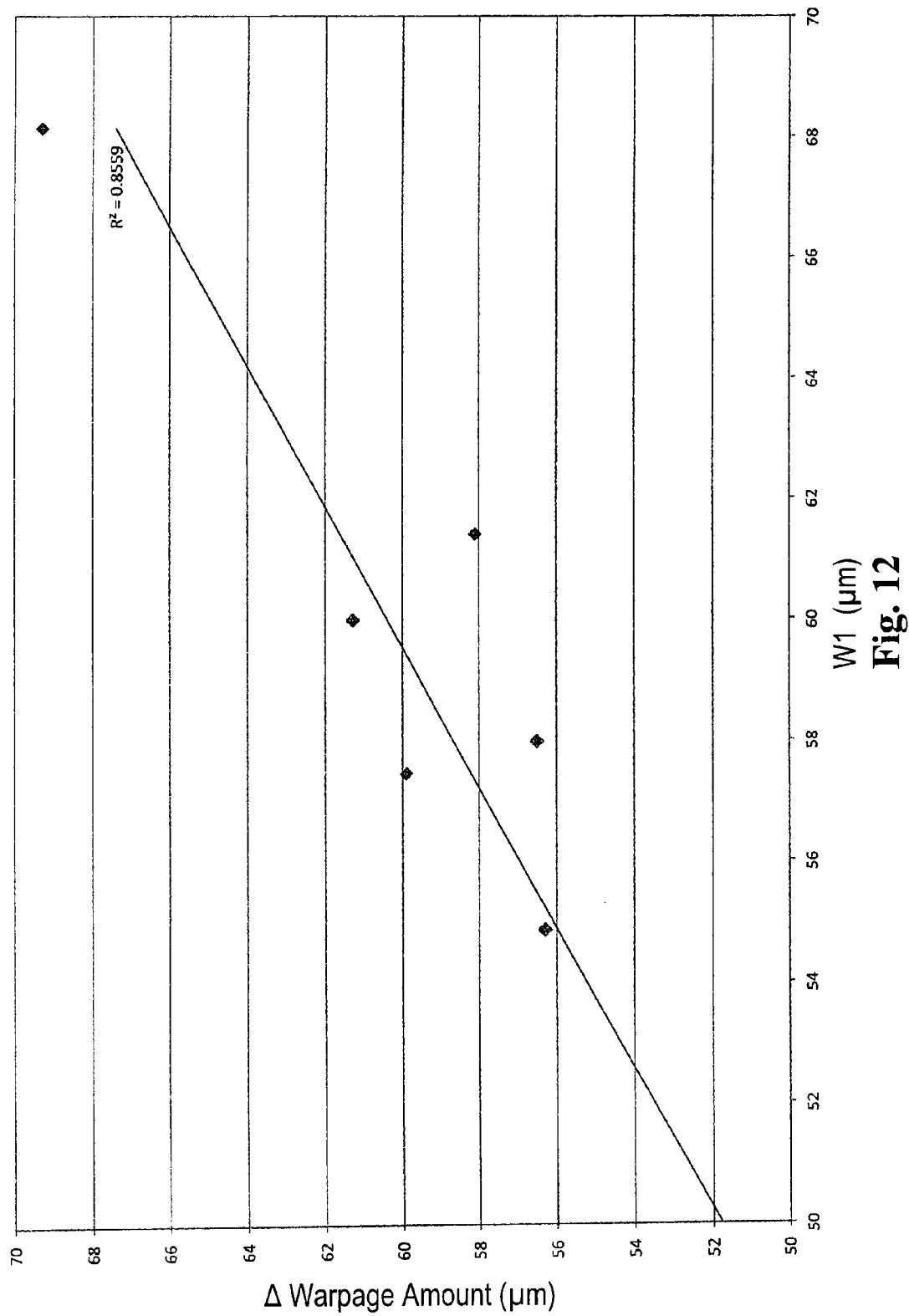
FIG. 12 shows a graph plotting W1 on the abscissa and Δwarpage amount on the ordinate.

FIG. 12 shows a graph plotting W1 on the abscissa and Δwarpage amount on the ordinate. It is seen from the graph shown in FIG. 12 that W1 has a correlation with the Δwarpage amount.

In formula (3-1), W1 is 56 or less, preferably 54 or less, 52 or less, or 50 or less. When W1 is 56 or less, even if a polishing treatment, etc. before chemical strengthening is simplified or omitted, warpage of the float glass after chemical strengthening can be reduced and excellent flatness can be obtained.

The hydrogen concentration and the Sn concentration in the bottom surface are adjusted by the method described later in (A) of "7. Production Method of Glass", whereby W1 in formula (3-1) can be adjusted. Specifically, it is preferable, for example, to decrease the $Na_2O$ concentration in the top surface by spraying water vapor or $SO_2$ gas onto the top surface at the time of annealing the glass, increase the $Na_2O$ concentration in the bottom surface by lowering the flow rate of $SO_2$ gas sprayed onto the bottom surface for the purpose of scratch prevention, or decrease the invasion amount of Sn into the bottom surface by lowering the temperature upstream of the float bath or increasing the hydrogen concentration in the atmosphere.

(4) Correlation of Ion Exchange Amount Difference Between Top Surface and Bottom Surface and Hydrogen Concentration Difference Between Top Surface and Bottom Surface Before Chemical Strengthening with ΔWarpage Amount The ion exchange amount is thought to be a stress generation factor, and the hydrogen concentration in the glass surface layer is thought to be a stress relaxation factor.

Namely, it is considered that as the hydrogen concentration in the glass surface layer is increased, the density of glass decreases. Since H in glass is present in the state of SiOH and the SiOH is produced resulting from breakage of a continuous crosslinked structure Si—O—Si in the glass, an increase in the hydrogen concentration in the glass surface layer is considered to cause a decrease in the density of glass, leading to stress relaxation.

The warpage of glass after chemical strengthening is thought to be attributable to the unbalance of stress difference between the top surface and the bottom surface and therefore, the value obtained by dividing the ion exchange amount by the hydrogen concentration is thought to have a correlation with the warpage amount.

Figure 8:
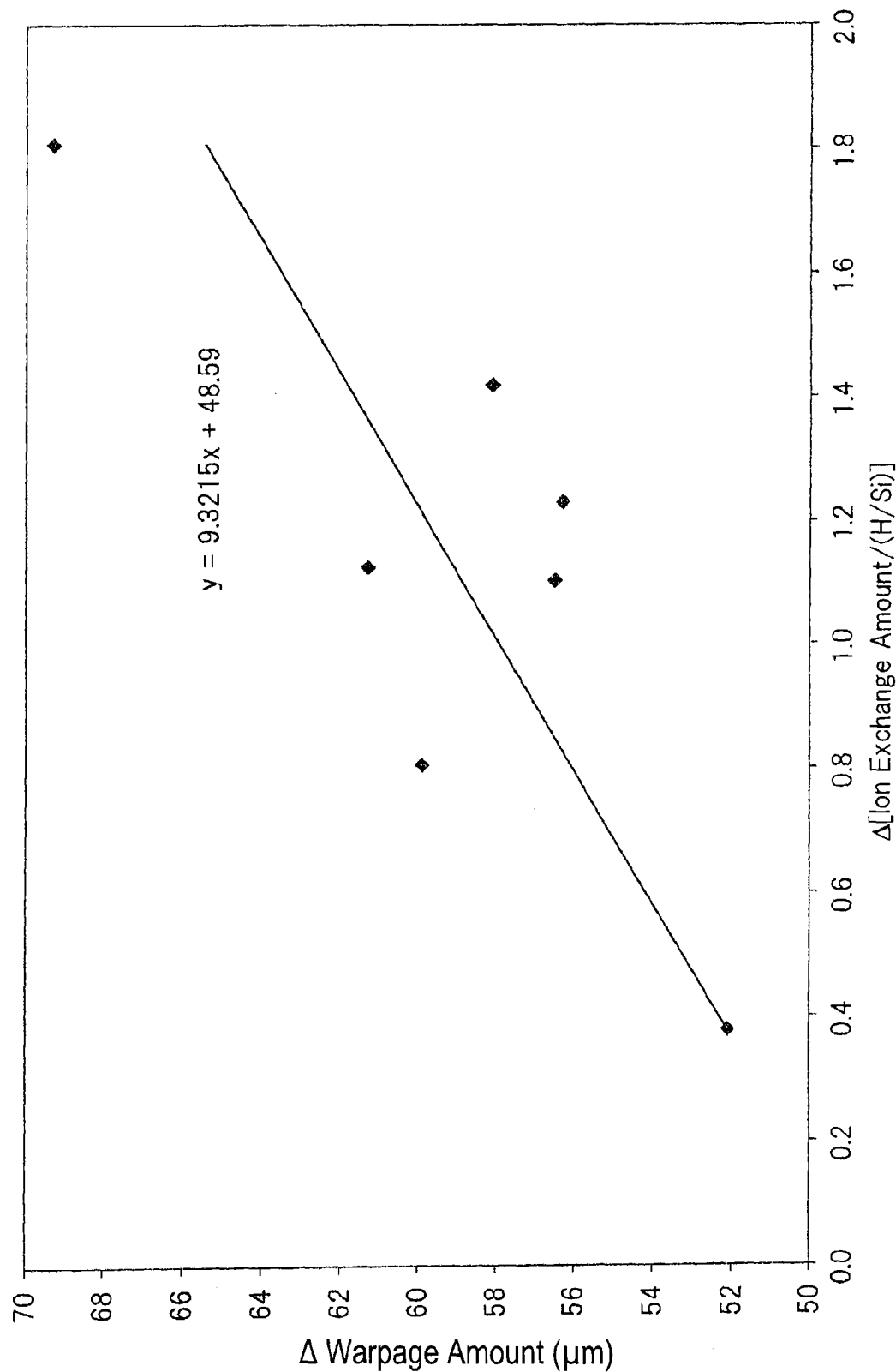
FIG. 8 is a graph plotting, on the abscissa, the difference between values obtained by dividing the ion exchange amounts in top surface and bottom surface by the hydrogen concentration, and on the ordinate, Δwarpage amount.

FIG. 8 shows a graph plotting, on the abscissa, the difference between values obtained by dividing the ion exchange amounts in the top surface and the bottom surface by the normalized hydrogen concentrations in the top surface and the bottom surface before chemical strengthening, respectively, and on the ordinate, Δwarpage amount.

It is seen from the graph shown in FIG. 8 that the difference in the values obtained by dividing the ion exchange amounts (ion exchange amount) in the top surface and the bottom surface by the normalized hydrogen concentrations (H/Si) in the top surface and the bottom surface before chemical strengthening, respectively, and the Δwarpage amount have a correlation represented by the following formula (4-1).

In addition, when multiple regression analysis is performed using, as factors, the normalized hydrogen concentration, ion exchange amount difference and Δwarpage amount, the following formula (4-1) is obtained.

$$W2=9.18 \times \Delta[(\text{ion exchange amount})/(H/Si)]+49 \quad \text{formula (4-1)}$$

In formula (4-1), the Δ[(ion exchange amount)/(H/Si)] is a value determined by subtracting a value that is obtained by dividing the ion exchange amount in the bottom surface by the normalized hydrogen concentration H/Si thereof, from a value that is obtained by dividing the ion exchange amount in the top surface by the normalized hydrogen concentration H/Si thereof.

In formula (4-1), the ion exchange amount is obtained according to the above-mentioned formula (2-1).

Figure 13:
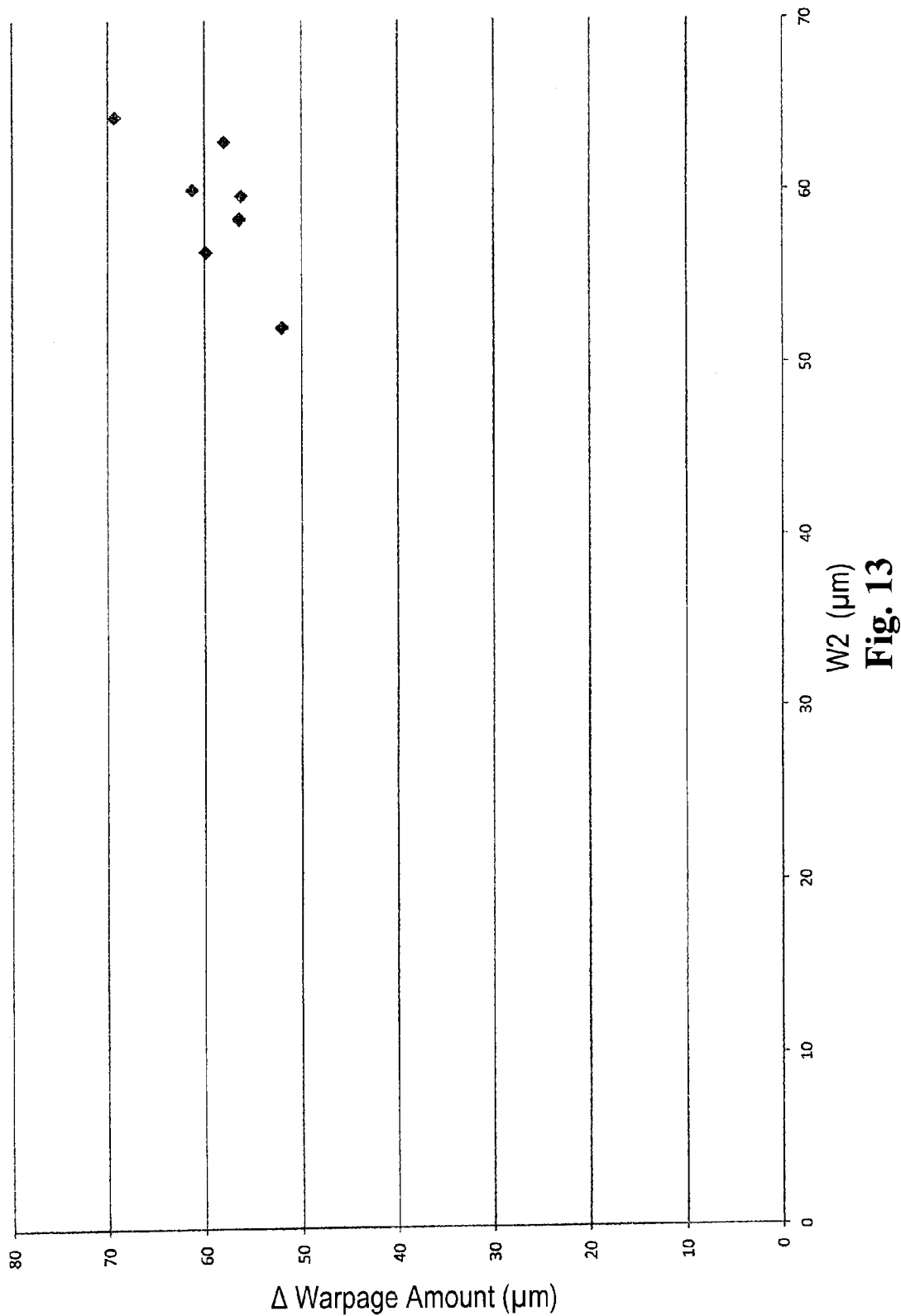
FIG. 13 shows a graph plotting W2 on the abscissa and Δwarpage amount on the ordinate.

FIG. 13 shows a graph plotting W2 on the abscissa and Δwarpage amount on the ordinate. It is seen from the graph shown in FIG. 13 that W2 has a correlation with the Δwarpage amount.

In formula (4-1), the absolute value of W2 is 56 or less, preferably 54 or less, 52 or less, or 50 or less. When W2 is 56 or less, even if a polishing treatment, etc. before chemical strengthening is simplified or omitted, warpage of the float glass after chemical strengthening can be reduced and excellent flatness can be obtained.

The hydrogen concentration is adjusted by the method described later in (A) of "7. Production Method of Glass", whereby W2 in formula (4-1) can be adjusted. Specifically, it is preferable, for example, to decrease the $Na_2O$ concentration in the top surface by spraying water vapor or $SO_2$ gas onto the top surface at the time of annealing the glass, increase the $Na_2O$ concentration in the bottom surface by lowering the flow rate of $SO_2$ gas sprayed onto the bottom surface for the purpose of scratch prevention, or decrease the invasion amount of Sn into the bottom surface by lowering the temperature upstream of the float bath or increasing the hydrogen concentration in the atmosphere.

(5) $Na_2O$ Concentration Difference and Sn Concentration Difference Between Top Surface and Bottom Surface Before Chemical Strengthening and ΔWarpage Amount In order to control warpage of a soda-lime glass after chemical strengthening, it is important to control the weathering degree of the glass surface layer and Sn concentration before chemical strengthening, and therefore, the $Na_2O$ concentration difference and Sn concentration difference in the top surface and the bottom surface before chemical strengthening are considered to have a correlation with the Δwarpage amount.

Figure 9:
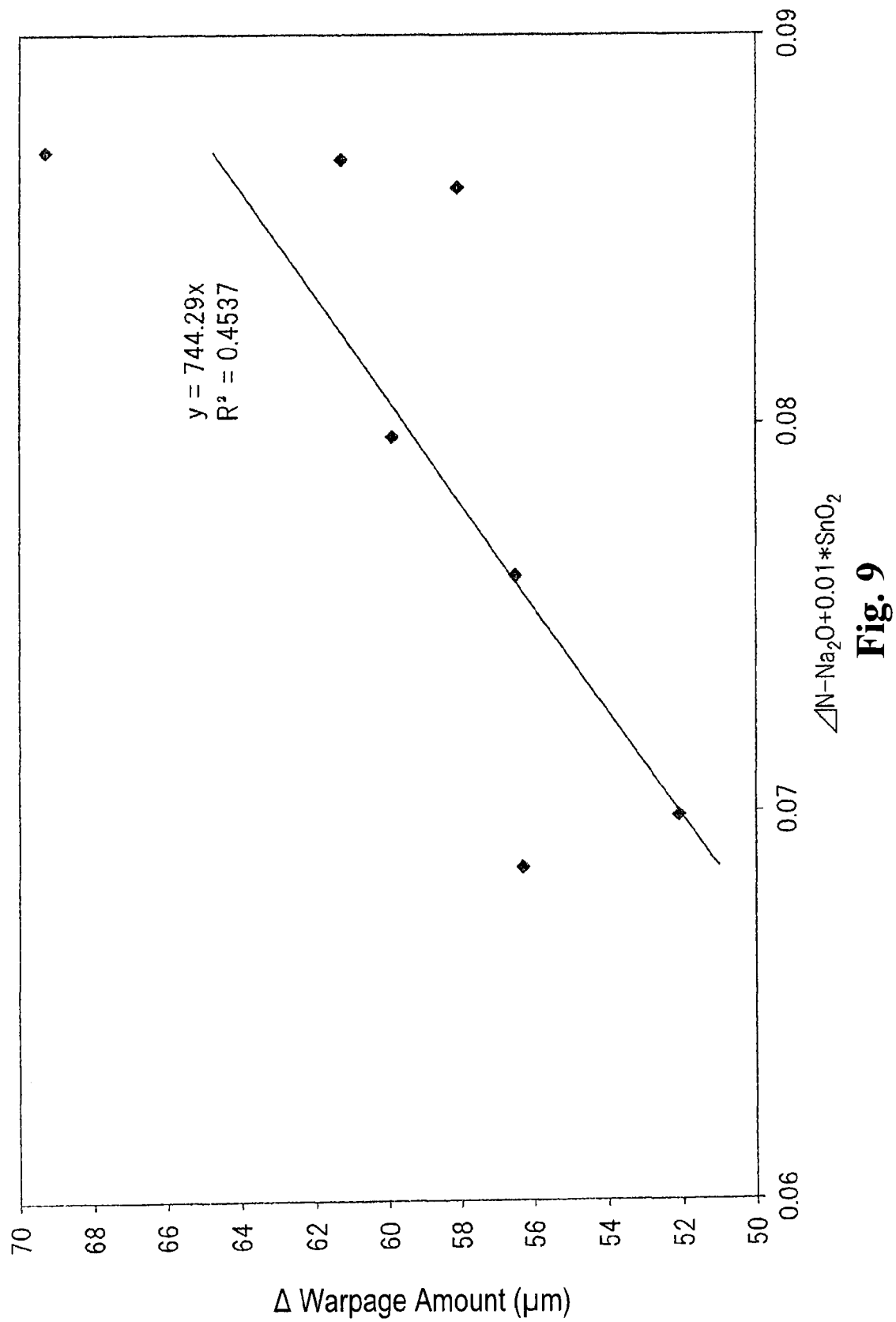
FIG. 9 is a graph showing the results of multiple regression analysis using, as factors, the normalized Na$_2$O surface concentration difference (ΔNa$_2$O) and Sn concentration difference (deposition amount per unit area) in the top surface and bottom surface before chemical strengthening, and the Δwarpage amount.

When multiple regression analysis is performed using, as factors, the normalized $Na_2O$ surface concentration difference (ΔN—$Na_2O$) and Sn concentration difference between the top surface and the bottom surface before chemical strengthening and the Δwarpage amount, as shown in FIG. 9, the normalized $Na_2O$ surface concentration difference and Sn concentration difference between the top surface and the bottom surface before chemical strengthening have a correlation represented by the following formula (5-1).

$$W3=744 \times [(\Delta N—Na_2O)+0.01 \times (\text{Sn concentration difference})] \quad \text{formula (5-1)}$$

In formula (5-1), the ΔN—$Na_2O$ is the difference in the normalized $Na_2O$ surface concentrations that are values obtained by dividing the $Na_2O$ concentrations at the surface in the top surface and the bottom surface of glass to be subjected to chemical strengthening by the $Na_2O$ concentrations at a depth position of 100 respectively, and is determined according to the following formula (5-2). Here, each $Na_2O$ concentration is a value measured by fluorescent X-ray analysis using an Na-Kα ray.

$$\Delta N—Na_2O=(\text{normalized } Na_2O \text{ surface concentration in top surface})-(\text{normalized } Na_2O \text{ surface concentration in bottom surface}) \quad \text{formula (5-2)}$$

In addition, the Sn concentration difference is an Sn concentration difference between the top surface and the bottom surface before chemical strengthening and is the difference obtained by subtracting the Sn deposition amount (unit: as $SnO_2 \mu g/cm^2$) per unit area of the top surface from the Sn deposition amount (unit: as $SnO_2 \mu g/cm^2$) per unit area of the bottom surface, and in the case where the glass does not contain $SnO_2$, this is equivalent to the Sn deposition amount per unit area of the bottom surface.

Figure 14:
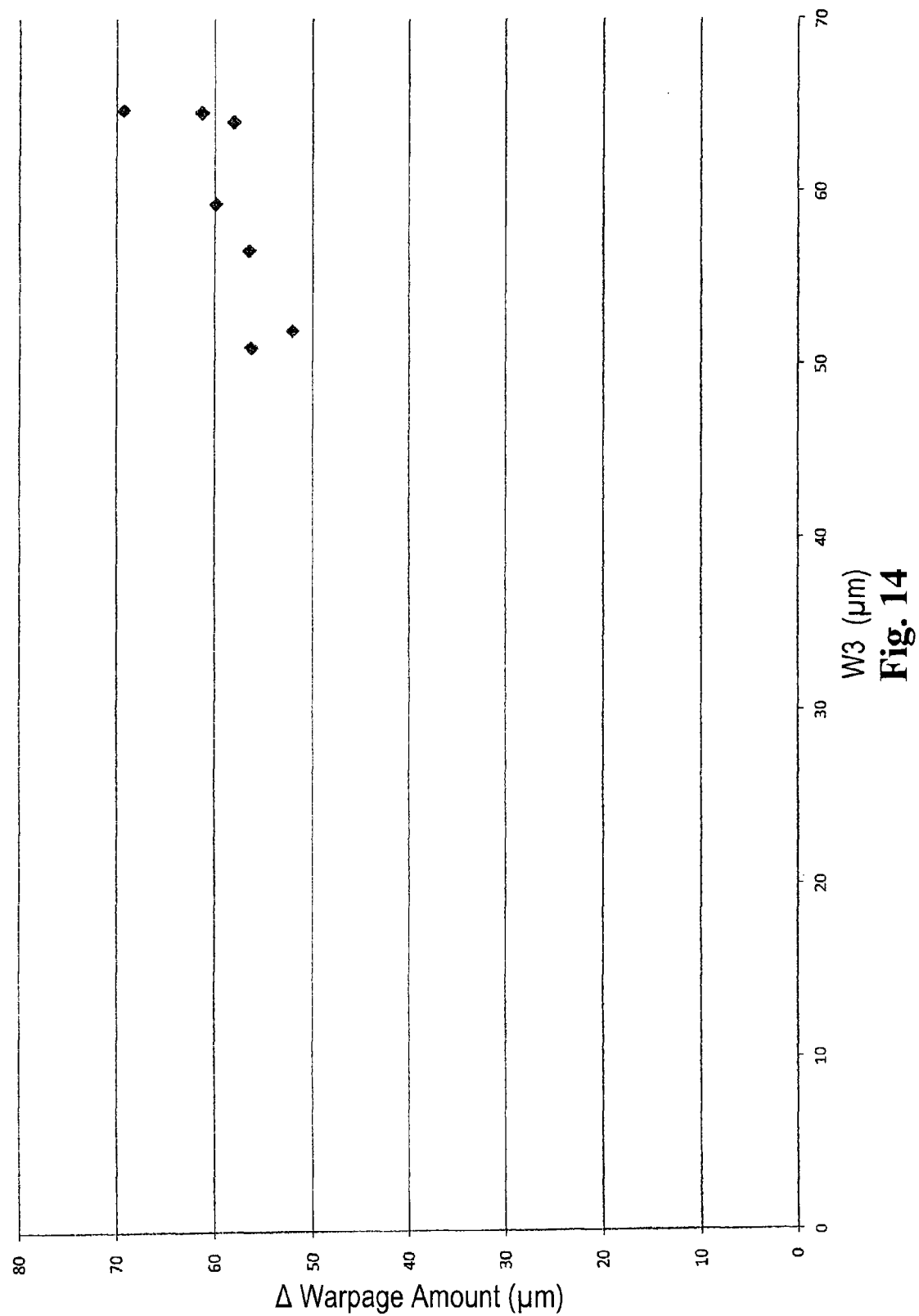
FIG. 14 shows a graph plotting W3 on the abscissa and Δwarpage amount on the ordinate.

FIG. 14 shows a graph plotting W3 on the abscissa and Δwarpage amount on the ordinate. It is seen from the graph shown in FIG. 14 that W3 has a correlation with the Δwarpage amount.

In formula (5-1), W3 is 58 or less, preferably 56 or less, 54 or less, or 52 or less. When W3 is 58 or less, even if a polishing treatment, etc. before chemical strengthening is simplified or omitted, warpage of the float glass after chemical strengthening can be reduced and excellent flatness can be obtained.

The $Na_2O$ concentration difference and the Sn concentration difference are adjusted by the method described later in (A) of "7. Production Method of Glass", whereby W3 in formula (5-1) can be adjusted. Specifically, it is preferable, for example, to decrease the $Na_2O$ concentration in the top surface by spraying water vapor or $SO_2$ gas onto the top surface at the time of annealing the glass, increase the $Na_2O$ concentration in the bottom surface by lowering the flow rate of $SO_2$ gas sprayed onto the bottom surface for the purpose of scratch prevention, or decrease the invasion amount of Sn into the bottom surface by lowering the temperature upstream of the float bath or increasing the hydrogen concentration in the atmosphere.

(6) Ion Exchange Amount (Hydrogen Concentration, $Na_2O$ Concentration and Sn Concentration) Difference and ΔWarpage Amount The ion exchange amount difference between the top surface and the bottom surface affects the warpage of glass after chemical strengthening, and the hydrogen concentration, $Na_2O$ concentration and Sn concentration are considered to be responsible for the ion exchange amount. Accordingly, with the normalized hydrogen concentration, normalized $Na_2O$ surface concentration and Sn concentration, the ion exchange amount shows a correlation represented by the following formula (6-1)

$$\text{Ion exchange amount } 2 = -0.02 \times (H/Si) + 5.54 \times (N - Na_2O \text{ concentration}) - 0.037 \times (Sn \text{ concentration}) \quad \text{formula (6-1)}$$

Figure 15:
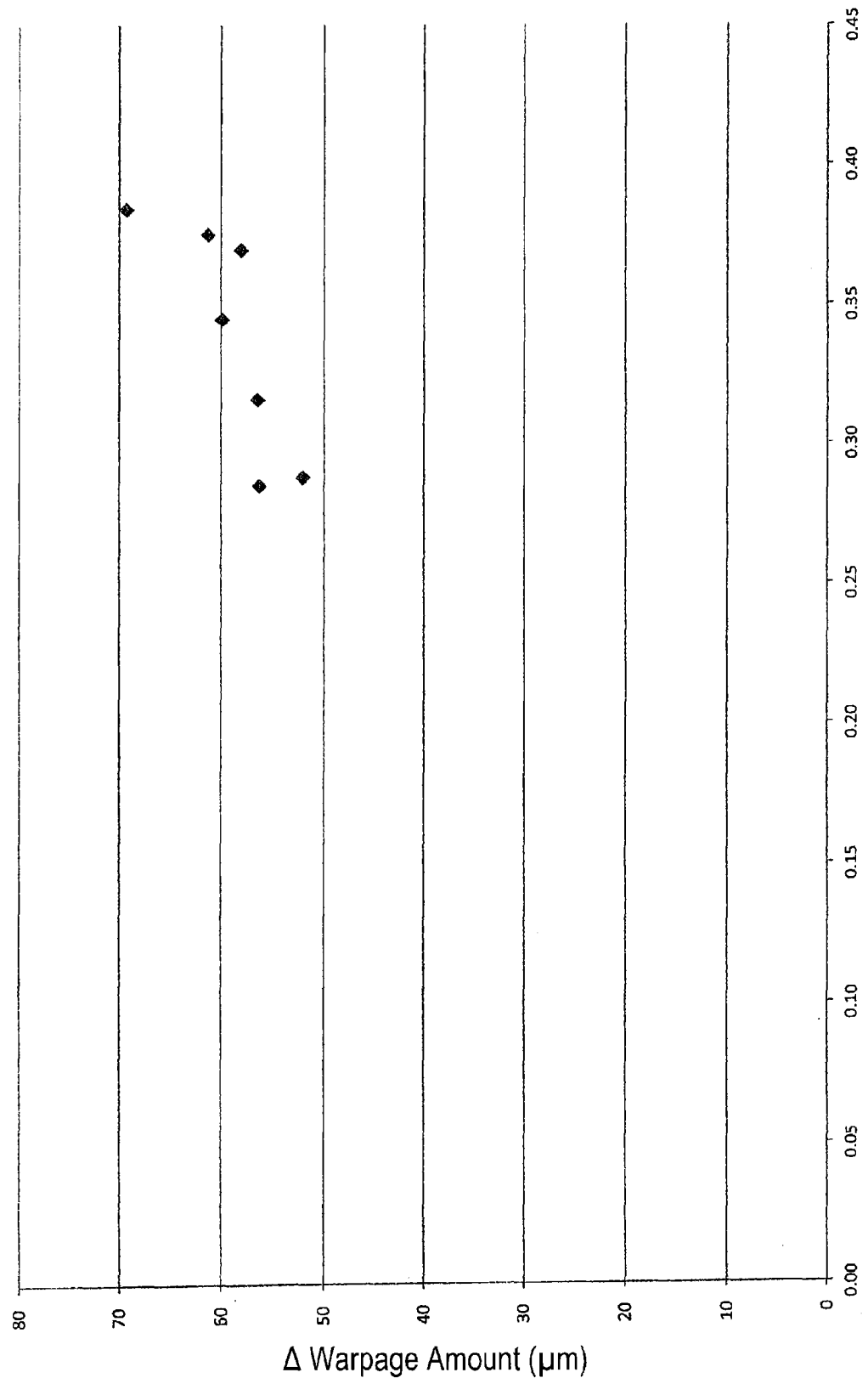
FIG. 15 shows a graph plotting, on the abscissa, the difference (Δion exchange amount 2) between ion exchange amounts 2 in top surface and bottom surface, and on the ordinate, Δwarpage amount.

FIG. 15 shows a graph plotting, on the abscissa, the difference (Δion exchange amount 2) between ion exchange amounts 2 in top surface and bottom surface, and on the ordinate, Δwarpage amount. It is seen from the graph shown in FIG. 15 that the Δion exchange amount 2 and the Δwarpage amount have a correlation.

The Δion exchange amount 2 is a value determined according to the following formula (6-2)

$$\Delta \text{Ion exchange amount } 2 = (\Delta \text{ion exchange amount } 2 \text{ in top surface}) - (\Delta \text{ion exchange amount } 2 \text{ in bottom surface}) \quad \text{formula (6-2)}$$

In formula (6-1), the Δion exchange amount 2 is 0.33 or less, preferably 0.31 or less, 0.29 or less, or 0.27 or less. When the Δion exchange amount 2 is 0.33 or less, even if a polishing treatment, etc. before chemical strengthening is simplified or omitted, warpage of the float glass after chemical strengthening can be reduced and excellent flatness can be obtained.

The hydrogen concentration, $Na_2O$ concentration and Sn concentration are adjusted by the method described later in (A) of "7. Production Method of Glass", whereby the ion exchange amount 2 in formula (6-1) can be adjusted. Specifically, it is preferable, for example, to decrease the $Na_2O$ concentration in the top surface by spraying water vapor or $SO_2$ gas onto the top surface at the time of annealing the glass, increase the $Na_2O$ concentration in the bottom surface by lowering the flow rate of $SO_2$ gas sprayed onto the bottom surface for the purpose of scratch prevention, or decrease the invasion amount of Sn into the bottom surface by lowering the temperature upstream of the float bath or increasing the hydrogen concentration in the atmosphere.

7. Production Method of Glass

The method for reducing the Δwarpage amount by achieving a small difference in the weathering degrees between the top surface and the bottom surface of a float glass and a small difference in the amounts of metal invading the glass surface put into contact with a molten metal at the time of float forming includes, for example, methods described in the following (A) to (D). These methods may be used individually or in combination.

(A) At the time of annealing a glass coming out of a float bath, by spraying $SO_2$ gas onto the glass, the alkali component $Na_2O$ of the glass is taken out from the glass as $Na_2SO_4$. By adjusting the amount of $SO_2$ gas sprayed onto the glass, the amounts of alkali in the top surface and the bottom surface can be adjusted to the same level, and the difference in the weathering degree of glass can be reduced.

(B) Water vapor is sprayed on the top surface side of glass in a lehr.

(C) The residence time of molten glass in a float bath is shortened.

(D) The temperature in the upstream region of a float bath is lowered.

The present invention is described below based on the drawings, but the present invention is not limited thereto. FIG. 10 is a longitudinal cross-sectional view of a production apparatus for a float glass of the present invention. In FIG. 10, 12 is a tweel, 22 is a fixed refractory located below the tweel, and 23 is a spout lip.

Although omitted in the drawing, a raw material is continuously fed to a glass tank furnace to melt the raw material in a high temperature region inside the glass tank furnace, and the molten glass obtained is guided to a cooling region to control the temperature. The molten glass 1 at the controlled temperature passes through a connection groove 11, passes through a space 2 formed by the tweel 12 and the fixed refractory 22 located therebelow, then fed to a molten metal bath 5 through the spout lip 23, and formed into a glass ribbon 4.

The sheet thickness of the float glass is preferably 1.5 mm or less, more preferably 1.1 mm or less. In addition, although it is typically 0.7 mm or more, a glass thinner than that is also used, if desired.

The float glass for chemical strengthening of the present invention can reduce the warpage after chemical strengthening irrespective of the composition. The composition of the float glass for chemical strengthening includes, for example, the following glass compositions.

(i) A glass having a composition containing, in mass %, from 60 to 80% of $SiO_2$, from 0.01 to 8% of $Al_2O_3$, from 8 to 22% of $Na_2O$, from 0 to 7% of $K_2O$, from 5 to 25% in total of RO (R=Mg, Ca, Sr, Ba), and from 0 to 5% of $ZrO_2$.

(ii) A glass having a composition containing, in mass %, from 64 to 77% of $SiO_2$, from 0.01 to 7% of $Al_2O_3$, from 10 to 18% of $Na_2O$, from 0 to 5% of $K_2O$, from 1 to 10% of MgO, from 1 to 12% of CaO, from 0 to 5% of SrO, from 0 to 5% of BaO, and from 0 to 3% of $ZrO_2$.

(iii) A glass having a composition containing, in mass %, from 60 to 80% of $SiO_2$, from 0.01 to 8% of $Al_2O_3$, from 8 to 22% of $Na_2O$, from 0 to 7% of $K_2O$, and from 0 to 5% of $ZrO_2$, where in the case of containing MgO, CaO, SrO or BaO, the total of MgO, CaO, SrO and BaO contents is from 5 to 25% and the ratio $Na_2O/Al_2O_3$ of $Na_2O$ and $Al_2O_3$ contents is 1.5 or more.

(iv) A glass having a composition containing, in mass %, from 60 to 80% of $SiO_2$, from 0.01 to 8% of $Al_2O_3$, from 8 to 22% of $Na_2O$, from 0 to 7% of $K_2O$, and from 0 to 5% of $ZrO_2$, where in the case of containing MgO, CaO, SrO or BaO, the total of MgO, CaO, SrO and BaO contents is from 5 to 25% and the ratio $Na_2O/Al_2O_3$ of $Na_2O$ and $Al_2O_3$ contents is from 1.5 to 6.

(v) A glass having a composition containing, in mass %, from 60 to 80% of $SiO_2$, from 0.01 to 8% of $Al_2O_3$, from 8 to 22% of $Na_2O$, from 0 to 7% of $K_2O$, and from 0 to 5% of $ZrO_2$, where in the case of containing MgO, CaO, SrO or BaO, the total of MgO, CaO, SrO and BaO contents is from 5 to 25%, the total of CaO, SrO and BaO contents is from 1 to 7%, and the ratio $Na_2O/Al_2O_3$ of $Na_2O$ and $Al_2O_3$ contents is 1.5 or more.

The float glass formed is cut into a predetermined size by a cutter not shown and then chemically strengthened, whereby a chemically strengthened float glass can be obtained.

The chemical strengthening is a treatment of forming a compressive stress layer on a glass surface by ion exchange at a temperature not more than a glass transition temperature, where an alkali metal ion having a small ion radius (typically, Li ion or Na ion) in a glass surface is exchanged with an alkali ion having a larger ion radius (typically, K ion). The chemical strengthening treatment can be performed by a conventionally known method.

An example where the float glass of the present invention is chemically strengthened and then used as a cover glass for a flat panel display is described below. FIG. 11 is a cross-sectional view of a display device where a cover glass is disposed. In the following description, front/back and right/left are based on the direction of the arrow in the drawings.

As illustrated in FIG. 11, a display device 10 generally includes a display panel 20 provided in a housing 15, and a cover glass 30 provided to cover the entire surface of the display panel 20 and surround the front of the housing 15.

The cover glass 30 is disposed mainly for the purpose of improving the beauty and strength of the display device 10, preventing the impact damage and the like and is formed from one sheet-shaped glass having a whole shape of nearly planer shape. As illustrated in FIG. 11, the cover glass 30 may be disposed to be spaced (to have an air layer) from the display side (front side) of the display panel 20 or may be attached to the display side of the display panel 20 with an adhesive film (not shown) having translucency.

On the front surface of the cover glass 30, which emits light from the display panel 20, a functional film 41 is provided, and on the back surface where light from the display panel 20 enters, a functional film 42 is provided at a position corresponding to the display panel 20. In FIG. 11, the functional films 41 and 42 are provided on both surfaces, but not limited thereto, and they may be provided on the front surface or back surface or may be omitted.

The functional films 41 and 42 have a function, for example, of preventing reflection of surrounding light, preventing impact damage, shielding electromagnetic wave, blocking near infrared ray, correcting color tone, and/or enhancing scratch resistance, and the thickness, shape, etc. are appropriately selected according to usage. The functional films 41 and 42 are formed, for example, by attaching a resin-made film to the cover glass 30. Alternatively, they may be formed by a thin film formation method such as deposition method, sputtering method or CVD method.

The reference numeral 44 is a black layer and is, for example, a coating film formed by coating an ink containing a pigment particle on the cover glass 30 and subjecting it to ultraviolet irradiation or heating/firing and then cooling. The display panel, etc. is made invisible from the outside of the housing 15 and thereby the aesthetics of appearance is enhanced. The reference numeral 44 is not limited to a black layer and may be, for example, a white layer.

PRACTICAL EXAMPLES

Practical Examples of the present invention are specifically described below, but the present invention is not limited thereto.

Practical Example 1

[Production of Float Glass]

Glass having the following composition was produced by a float method to have a sheet thickness of 0.7 mm and cut into a size of 10 cm×10 cm to produce float glass plates of Examples 1 to 4.

Composition A:
  in mass %, $SiO_2$: 71.5%, $Al_2O_3$: 1.8%, $Na_2O$: 13.5%, $K_2O$: 0.26%, MgO: 4.64%, CaO: 7.83%, $ZrO_2$: 0.03%

Composition B:
  $SiO_2$: 71.5%, $Al_2O_3$: 1.8%, $Na_2O$: 13.5%, $K_2O$: 0.26%, MgO: 4.64%, CaO: 7.83%, $ZrO_2$: 0.03%

Composition C:
  $SiO_2$: 71.5%, $Al_2O_3$: 1.8%, $Na_2O$: 13.5%, $K_2O$: 0.26%, MgO: 4.64%, CaO: 7.83%, $ZrO_2$: 0.03%

[Evaluation Methods]

(1) Measurement of Hydrogen Concentration in Glass Surface Layer

The hydrogen concentration of each float glass of Practical Examples 1 and 2 and Comparative Examples 1 to 3 was analyzed down to a depth of 20 μm by secondary ion mass spectrometry. The [$^1H^-/^{30}Si^-$] profile of the float glass by secondary ion mass spectrometry is shown, and this profile can be regarded as equivalent to the hydrogen concentration profile.

Analysis conditions of the secondary ion mass spectrometry were as follows.

Measurement apparatus: ADEPT 1010, manufactured by Ulvac-Phi, Inc.
Primary ion species: $Cs^+$
Primary accelerating voltage: 5.0 kV
Primary ion current: 1 μA
Primary ion incident angle (angle from direction perpendicular to sample surface): 60°
Luster size: 200×200 μm$^2$
Detection region: 40×40 μm$^2$
Sputter rate: 14 nm/sec
Secondary ion polarity: minus
Electron gun for neutralization: used The [$^1H^-/^{30}Si^-$]'s at a depth of 0 to 10 μm and at a depth of 105 to 110 μm were measured, and the difference in the normalized intensities at a depth of 0 to 10 μm between the bottom surface (surface B) and the top surface (surface T) was calculated. In Table 1, "H/Si" indicates a value obtained by dividing the average value at a depth of 0 to 10 μm by the average value at a depth of 105 to 110 μm.

Here, field aperture of detector was 1, and ESA input lens of detector was 550.

(2) Measurement of Warpage Amount

After measuring the warpage amount by a contact-type surface profile analyzer (SURFCOM 1400D (trade name)) manufactured by Tokyo Seimitsu Co., Ltd. before chemical strengthening, each float glass was chemically strengthened with potassium nitrate molten salt at 425° C. for 150 minutes. The warpage amount after chemical strengthening was measured in the same manner, and the Δwarpage amount represented by (formula) Δwarpage amount=warpage amount after chemical strengthening−warpage amount before chemical strengthening was calculated. Here, the Δwarpage amount was the Δwarpage amount measured in a 9 cm-square float glass.

(3) Measurements of $Na_2O$ Concentration and $K_2O$ Concentration

As for the $Na_2O$ concentration and $K_2O$ concentration in the glass surface layer, the intensities of Na-Kα ray and K-Kα ray were measured respectively by fluorescent X-ray analysis by using ZSX Primus II manufactured by Rigaku Corporation, and the concentration was determined from the relative intensity ratio to the standard sample.

In Table 1, "N—$Na_2O$" is the normalized $Na_2O$ surface concentration that is a value obtained by dividing the $Na_2O$ concentration by the $Na_2O$ concentration at a depth position of 100 μm. Here, the $Na_2O$ concentration is a value calculated from the relative intensity ratio to a standard sample by measuring the intensity of Na-Kα ray by fluorescent X-ray analysis. The ion exchange amount ($K_2O$ concentration) after chemical strengthening is shown in the column of $K_2O$ Ion Exchange Amount in Table 1.

(4) Measurement of Sn Concentration

Regarding the Sn concentration in the glass surface, the glass surface was etched with a hydrofluoric acid solution and the Sn concentration in the solution was quantitatively determined by ICP emission spectrometry. As for the ICP emission spectrometry, SPS3100 manufactured by SII NanoTechnology Inc. was used.

In Table 1, the glass of Compositions A to C does not contain $SnO_2$, and the $SnO_2$ concentration in the top surface was evidently 0 and therefore, was not measured. The same applies to Tables 2 to 6 below.

With respect to the glass of Examples 1 to 4, the normalized hydrogen concentration [0-10 μm average (H/Si)/105-110 μm (average H/Si)], N—$Na_2O$ concentration (surface concentration/concentration at depth position of 100 μm; hereinafter, also referred to as normalized $Na_2O$ surface concentration), $K_2O$ concentration and Sn concentration (deposition amount per unit area), before chemical strengthening, and the ion exchange amount ($K_2O$ concentration) and Δwarpage amount, after chemical strengthening, were determined, and the results are shown in Table 1.

The reason why the N—$Na_2O$ concentration in the top surface is less than 1 is considered because the $SO_2$ gas sprayed onto the bottom surface flowed around the top surface side. In addition, the reason why the N—$Na_2O$ concentration in the top surface differs, for example, between Example 1 and Example 4 is considered because the $SO_2$ gas spraying state fluctuated.

TABLE 1

| Composition | Example | Surface | Measurement Results Before Chemical Strengthening | | | | Measurement Results After Chemical Strengthening | |
|---|---|---|---|---|---|---|---|---|
| | | | H/Si | N—$Na_2O$ | $K_2O$ (wt %) | $SnO_2$ (μg/cm$^2$) | $K_2O$ Ion Exchange Amount (wt %) | ΔWarpage Amount (μm) |
| A | 1 | Top | 1.02 | 0.94 | 0.327 | — | 5.01 | 58 |
| | | Bottom | 1.35 | 0.91 | 0.323 | 6.18 | 4.71 | |
| B | 2 | Top | 1.53 | 0.93 | 0.310 | — | 4.93 | 52 |
| | | Bottom | 1.60 | 0.91 | 0.305 | 5.46 | 4.58 | |
| | 3 | Top | 1.54 | 0.93 | 0.305 | — | 4.89 | 60 |
| | | Bottom | 1.91 | 0.90 | 0.300 | 5.65 | 4.53 | |
| | 4 | Top | 1.23 | 0.92 | 0.269 | — | 5.39 | 57 |
| | | Bottom | 1.54 | 0.90 | 0.265 | 6.06 | 5.04 | |
| | 5 | Top | 1.27 | 0.92 | 0.268 | — | 5.35 | 69 |
| | | Bottom | 2.02 | 0.89 | 0.265 | 6.13 | 4.87 | |
| | 6 | Top | 1.24 | 0.92 | 0.282 | — | 5.35 | 56 |
| | | Bottom | 1.64 | 0.91 | 0.279 | 5.57 | 5.06 | |
| C | 7 | Top | 1.10 | 0.94 | 0.275 | — | 5.03 | 61 |
| | | Bottom | 1.38 | 0.91 | 0.272 | 6.05 | 4.74 | |

Practical Example 2

$Na_2O$ Concentration Difference in Top Surface and Bottom Surface Before Chemical Strengthening and ΔWarpage Amount Since the $Na_2O$ concentration difference between the top surface and the bottom surface of a soda-lime glass sheet before chemical strengthening is considered to have a correlation with the Δwarpage amount, the difference Δ(N—$Na_2O^2$) between squared normalized $Na_2O$ surface concentrations in the top surface and the bottom surface was determined from the data shown in Table 1, and the correlation with the Δwarpage amount was studied.

The results are shown in Table 2 and FIG. 6. FIG. 6 is a graph plotting, on the abscissa, the difference Δ(N—$Na_2O^2$) (Top-Bottom) between squared normalized $Na_2O$ surface concentrations in the top surface and the bottom surface of glass to be subjected to chemical strengthening, and on the ordinate, Δwarpage amount.

From the graph shown in FIG. 6, it was found that the difference Δ(N—$Na_2O^2$) between squared normalized $Na_2O$ surface concentrations in the top surface and the bottom surface of a soda-lime glass sheet before chemical strengthening and the Δwarpage amount have a correlation represented by the following formula (1-1).

$$\Delta\text{Warpage amount} = 370 \times \Delta(N-Na_2O^2) + 45 \quad \text{formula (1-1)}$$

In formula (1-1), the $\Delta(N-Na_2O^2)$ is the difference between squares of the values obtained by measuring, by fluorescent X-ray analysis, the normalized $Na_2O$ surface concentration in the top surface and the bottom surface of glass to be subjected to chemical strengthening and is determined according to the following formula (1-2)

$\Delta Na_2O$=(normalized $Na_2O$ surface concentration in top surface before chemical strengthening)$^2$−(normalized $Na_2O$ surface concentration in bottom surface before chemical strengthening)$^2$  formula (1-2)

It was understood from the results shown in Table 2 and FIG. 6 that when $\Delta(N-Na_2O^2)$ in formula (1-1) is 0.040 or less, the $\Delta$warpage amount can be 58 μm or less.

TABLE 2

| Example | Surface | N—Na₂O | N—Na₂O^2 | Δ(N—Na₂O^2) (Top − Bottom) | ΔWarpage Amount (μm) |
|---|---|---|---|---|---|
| 1 | Top | 0.94 | 0.881 | 0.045 | 58 |
|   | Bottom | 0.91 | 0.836 |  |  |
| 2 | Top | 0.93 | 0.865 | 0.028 | 52 |
|   | Bottom | 0.91 | 0.837 |  |  |
| 3 | Top | 0.93 | 0.859 | 0.042 | 60 |
|   | Bottom | 0.90 | 0.817 |  |  |
| 4 | Top | 0.92 | 0.847 | 0.028 | 57 |
|   | Bottom | 0.90 | 0.819 |  |  |
| 5 | Top | 0.92 | 0.838 | 0.046 | 69 |
|   | Bottom | 0.89 | 0.791 |  |  |
| 6 | Top | 0.92 | 0.852 | 0.024 | 56 |
|   | Bottom | 0.91 | 0.828 |  |  |
| 7 | Top | 0.94 | 0.877 | 0.049 | 61 |
|   | Bottom | 0.91 | 0.828 |  |  |

Practical Example 3

Ion Exchange Amount Difference Between Top Surface and Bottom Surface after Chemical Strengthening and $\Delta$Warpage Amount Since the ion exchange amount difference between the top surface and the bottom surface is considered to have a correlation with the $\Delta$warpage amount, the ion exchange amount difference ($\Delta$ion exchange amount 1) was determined from the data shown in Table 1, and the correlation with the $\Delta$warpage amount was studied.

The $\Delta$ion exchange amount 1 is a value obtained by subtracting the ion exchange amount 1 in the bottom surface from the ion exchange amount 1 in the top surface. The ion exchange amount 1 was determined according to the following formula (2-1).

Ion exchange amount 1=5.51×(normalized $Na_2O$ surface concentration)−0.038×(Sn concentration)  formula (2-1)

Ion exchange amount 1 difference=(ion exchange amount in top surface)−(ion exchange amount in bottom surface)  formula (2-2)

The results are shown in Table 3 and FIG. 7. FIG. 7 is a graph plotting, on the abscissa, the $\Delta$ion exchange amount 1 that is the difference in the ion exchange amount 1 between the top surface and the bottom surface, and on the ordinate, the $\Delta$warpage amount.

From the graph shown in FIG. 7, it was found that the $\Delta$ion exchange amount 1 and the $\Delta$warpage amount have a correlation represented by the following formula (2-3).

$\Delta$Warpage amount=103×($\Delta$ion exchange amount 1)+24  formula (2-3)

It was understood from the results shown in Table 3 and FIG. 7 that when $\Delta$ion exchange amount 1 is 0.32 or less, the $\Delta$warpage amount can be 58 μm or less.

TABLE 3

| Example | Surface | N—Na₂O | SnO₂ (μg/cm²) | Ion Exchange Amount | ΔIon Exchange Amount | ΔWarpage Amount (μm) |
|---|---|---|---|---|---|---|
| 1 | Top | 0.94 | — | 5.18 | 0.37 | 58 |
|   | Bottom | 0.91 | 6.18 | 4.81 |  |  |
| 2 | Top | 0.93 | — | 5.13 | 0.29 | 52 |
|   | Bottom | 0.91 | 5.46 | 4.83 |  |  |
| 3 | Top | 0.93 | — | 5.11 | 0.34 | 60 |
|   | Bottom | 0.90 | 5.65 | 4.77 |  |  |
| 4 | Top | 0.92 | — | 5.07 | 0.32 | 57 |
|   | Bottom | 0.90 | 6.06 | 4.76 |  |  |
| 5 | Top | 0.92 | — | 5.05 | 0.38 | 69 |
|   | Bottom | 0.89 | 6.13 | 4.67 |  |  |
| 6 | Top | 0.92 | — | 5.09 | 0.28 | 56 |
|   | Bottom | 0.91 | 5.57 | 4.80 |  |  |
| 7 | Top | 0.94 | — | 5.16 | 0.38 | 61 |
|   | Bottom | 0.91 | 6.05 | 4.79 |  |  |

Practical Example 4

Hydrogen Concentration Difference and Sn Concentration Difference Between Top Surface and Bottom Surface Before Chemical Strengthening, Ion Exchange Amount Difference, and $\Delta$Warpage Amount Since a correlation is considered to exist among the hydrogen concentration difference and Sn concentration difference between the top surface and the bottom surface before chemical strengthening, the ion exchange amount difference and the $\Delta$warpage amount, multiple regression analysis was performed based on the data shown in Table 1 by using these values as factors and, as a result, the following formula (3-1) was obtained. The data obtained from the data shown in Table 1 is shown in Table 4.

W1=−16×($\Delta$H/Si)−6.47×(Sn concentration difference)−43.8×($\Delta$ion exchange amount 1)  formula (3-1)

In formula (3-1), $\Delta$H/Si is the difference (difference in the normalized hydrogen concentration) between values obtained by measuring, by SIMS analysis, the hydrogen concentration difference between the top surface and the bottom surface before chemical strengthening and is determined according to the following formula (3-2).

$\Delta$H/Si=(normalized hydrogen concentration in top surface before chemical strengthening)−(normalized hydrogen concentration in bottom surface before chemical strengthening)  formula (3-2)

The $\Delta$ion exchange amount 1 is a value obtained by subtracting the ion exchange amount in the bottom surface from the ion exchange amount in the top surface. The ion exchange amount is determined according to the above-mentioned formula (2-1).

FIG. 12 shows a graph plotting W1 on the abscissa and $\Delta$warpage amount on the ordinate. The graph shown in FIG. 12 revealed that W1 has a correlation with the $\Delta$warpage amount. It was understood from the results shown in Table 4 and FIG. 12 that when W1 is 56 or less, the $\Delta$warpage amount can be 58 μm or less.

TABLE 4

| Example | Surface | H/Si | Δ(H/Si) | N—Na$_2$O | SnO$_2$ (μg/cm$^2$) | Ion Exchange Amount | ΔIon Exchange Amount | W1 (μm) | ΔWarpage Amount (μm) |
|---|---|---|---|---|---|---|---|---|---|
| 1 | Top | 1.02 | −0.33 | 0.94 | — | 5.18 | 0.37 | 61 | 58 |
|   | Bottom | 1.35 |   | 0.91 | 6.18 | 4.81 |   |   |   |
| 2 | Top | 1.53 | −0.08 | 0.93 | — | 5.13 | 0.29 | 49 | 52 |
|   | Bottom | 1.60 |   | 0.91 | 5.46 | 4.83 |   |   |   |
| 3 | Top | 1.54 | −0.37 | 0.93 | — | 5.11 | 0.34 | 57 | 60 |
|   | Bottom | 1.91 |   | 0.90 | 5.65 | 4.77 |   |   |   |
| 4 | Top | 1.23 | −0.31 | 0.92 | — | 5.07 | 0.32 | 58 | 57 |
|   | Bottom | 1.54 |   | 0.90 | 6.06 | 4.76 |   |   |   |
| 5 | Top | 1.27 | −0.75 | 0.92 | — | 5.05 | 0.38 | 68 | 69 |
|   | Bottom | 2.02 |   | 0.89 | 6.13 | 4.67 |   |   |   |
| 6 | Top | 1.24 | −0.40 | 0.92 | — | 5.09 | 0.28 | 55 | 56 |
|   | Bottom | 1.64 |   | 0.91 | 5.57 | 4.80 |   |   |   |
| 7 | Top | 1.10 | −0.28 | 0.94 | — | 5.16 | 0.38 | 60 | 61 |
|   | Bottom | 1.38 |   | 0.91 | 6.05 | 4.79 |   |   |   |

Practical Example 5

Ion Exchange Amount Difference Between Top Surface and Bottom Surface, Hydrogen Concentration Difference Between Top Surface and Bottom Surface Before Chemical Strengthening and ΔWarpage Amount Since a correlation is considered to exist among the ion exchange amount difference between the top surface and the bottom surface, the hydrogen concentration difference between the top surface and the bottom surface before chemical strengthening and the Δwarpage amount, the correlation among the ion exchange amount difference between the top surface and the bottom surface, the hydrogen concentration difference between the top surface and the bottom surface before chemical strengthening, and the Δwarpage amount was studied from the data shown in Table 1.

The results are shown in Table 5 and FIG. 8. FIG. 8 is a graph plotting, on the abscissa, a value obtained by dividing the ion exchange amount difference between the top surface and the bottom surface by the hydrogen concentration difference between the top surface and the bottom surface before chemical strengthening, and on the ordinate, the Δwarpage amount.

In addition, since a correlation is considered to exist among the hydrogen concentration, the ion exchange amount and the Δwarpage amount, multiple regression analysis was performed based on the data shown in Table 1 by using these values as factors and, as a result, the following formula (4-1) was obtained.

$$W2 = 9.18 \times \Delta[(\text{ion exchange amount})/(H/Si)] + 49 \qquad \text{formula (4-1)}$$

In formula (4-1), the Δ[(ion exchange amount)/(H/Si)] is a value determined by subtracting a value obtained by dividing the ion exchange amount in the bottom surface by the normalized hydrogen concentration H/Si, from a value obtained by dividing the ion exchange amount in the top surface by the normalized hydrogen concentration H/Si. The ion exchange amount was determined according to the above formula (2-1).

FIG. 13 shows a graph plotting W2 on the abscissa and Δwarpage amount on the ordinate. The graph shown in FIG. 13 revealed that W2 has a correlation with the Δwarpage amount. It was understood from the results shown in Table 5 and FIG. 13 that when W2 is 56 or less, the Δwarpage amount can be 58 μm or less.

TABLE 5

| Example | Surface | H/Si | Ion Exchange Amount | Ion Exchange Amount/ (H/Si) | ΔIon Exchange Amount (H/Si) | W2 (μm) | ΔWarpage Amount (μm) |
|---|---|---|---|---|---|---|---|
| 1 | Top | 1.02 | 5.18 | 5.08 | 1.51 | 63 | 58 |
|   | Bottom | 1.35 | 4.81 | 3.56 |   |   |   |
| 2 | Top | 1.53 | 5.13 | 3.36 | 0.35 | 52 | 52 |
|   | Bottom | 1.60 | 4.83 | 3.01 |   |   |   |
| 3 | Top | 1.54 | 5.11 | 3.32 | 0.82 | 57 | 60 |
|   | Bottom | 1.91 | 4.77 | 2.50 |   |   |   |
| 4 | Top | 1.23 | 5.07 | 4.11 | 1.03 | 58 | 57 |
|   | Bottom | 1.54 | 4.76 | 3.09 |   |   |   |
| 5 | Top | 1.27 | 5.05 | 3.98 | 1.67 | 64 | 69 |
|   | Bottom | 2.02 | 4.67 | 2.31 |   |   |   |
| 6 | Top | 1.24 | 5.09 | 4.10 | 1.17 | 60 | 56 |
|   | Bottom | 1.64 | 4.80 | 2.92 |   |   |   |
| 7 | Top | 1.10 | 5.16 | 4.69 | 1.21 | 60 | 61 |
|   | Bottom | 1.38 | 4.79 | 3.48 |   |   |   |

Practical Example 6

Na$_2$O Concentration Difference and Sn Concentration Difference Between Top Surface and Bottom Surface Before Chemical Strengthening, and ΔWarpage Amount Since the normalized Na$_2$O surface concentration difference and Sn concentration difference between the top surface and the bottom surface before chemical strengthening are considered to have a correlation with the Δwarpage amount, multiple regression analysis was performed based on the data shown in Table 1 by using these values as factors. The results are shown in Table 6, FIG. 9 and FIG. 17.

Figure 17:
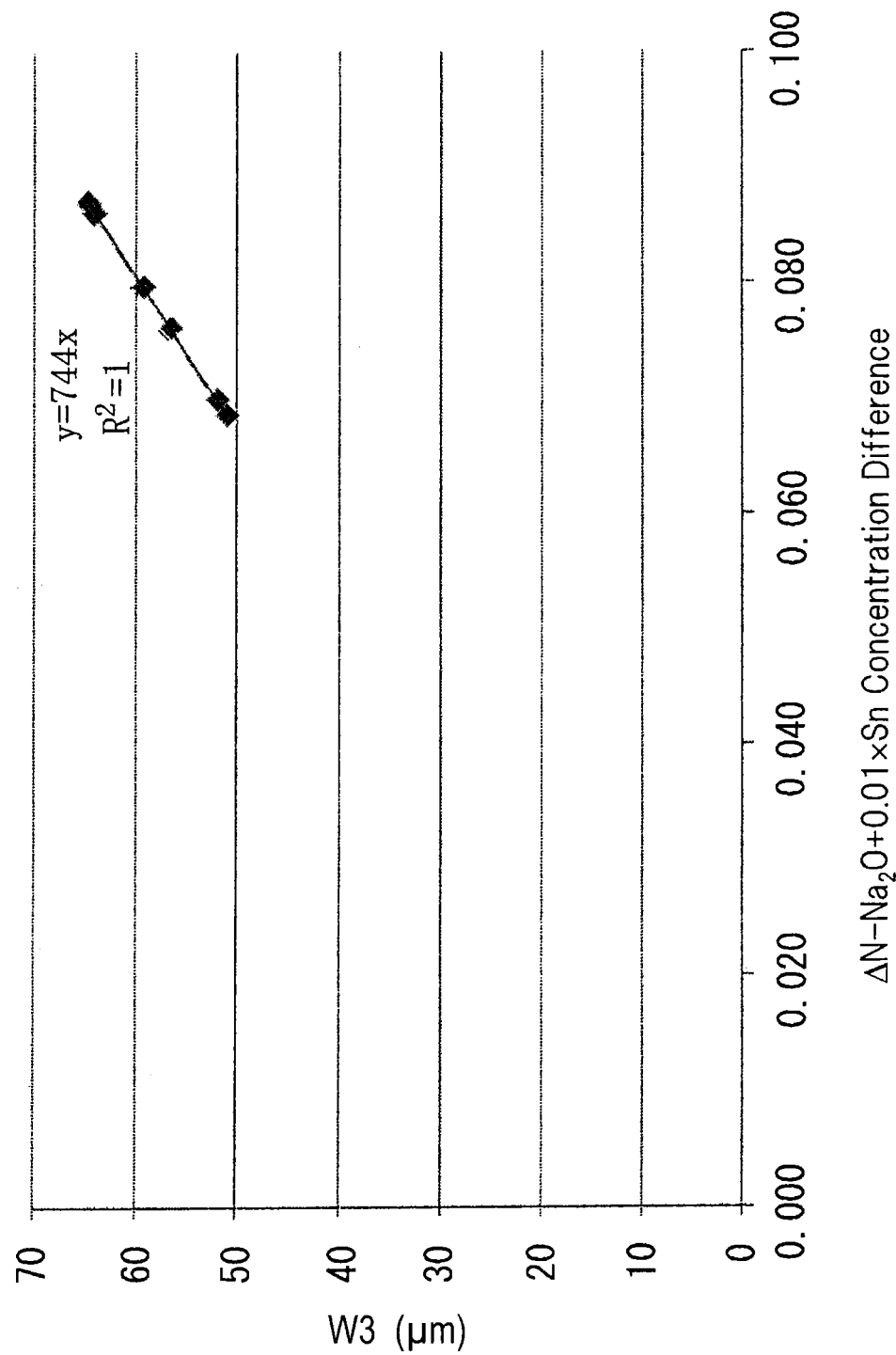
FIG. 17 shows a graph plotting [(ΔN—Na$_2$O)+0.01×(Sn concentration difference)] on the abscissa and W3 on the ordinate.

As shown in FIG. 17, it was found that the normalized Na$_2$O surface concentration difference and Sn concentration difference between the top surface and the bottom surface before chemical strengthening have a correlation represented by the following formula (5-1).

$$W3 = 744 \times [(\Delta N\text{—}Na_2O) + 0.01 \times (\text{Sn concentration difference})] \qquad \text{formula (5-1)}$$

In formula (5-1), the ΔN—Na$_2$O is a value obtained by subtracting the normalized Na$_2$O surface concentration in the bottom surface from the normalized Na$_2$O surface concentration in the top surface and is obtained according to the following formula (5-2).

ΔN—Na$_2$O = (normalized Na$_2$O surface concentration in top surface before chemical strengthening) − (normalized Na$_2$O surface concentration in bottom surface before chemical strengthening)     formula (5-2)

FIG. 14 shows a graph plotting W3 on the abscissa and Δwarpage amount on the ordinate. The graph shown in FIG. 14 revealed that W3 has a correlation with the Δwarpage amount. It was understood from the results shown in Table 6 and FIG. 14 that when W3 is 58 or less, the Δwarpage amount can be 58 μm or less.

TABLE 6

| Example | Surface | N—Na$_2$O | ΔN—Na$_2$O | SnO$_2$ (μg/cm$^2$) | ΔN—Na$_2$O + 0.01*SnO$_2$ | W3 (μm) | ΔWarpage Amount (μm) |
|---|---|---|---|---|---|---|---|
| 1 | Top | 0.94 | 0.024 | 6.18 | 0.086 | 64 | 58 |
|   | Bottom | 0.91 | | | | | |
| 2 | Top | 0.93 | 0.015 | 5.46 | 0.070 | 52 | 52 |
|   | Bottom | 0.91 | | | | | |
| 3 | Top | 0.93 | 0.023 | 5.65 | 0.080 | 59 | 60 |
|   | Bottom | 0.90 | | | | | |
| 4 | Top | 0.92 | 0.015 | 6.06 | 0.076 | 57 | 57 |
|   | Bottom | 0.90 | | | | | |
| 5 | Top | 0.92 | 0.026 | 6.13 | 0.087 | 65 | 69 |
|   | Bottom | 0.89 | | | | | |
| 6 | Top | 0.92 | 0.013 | 5.57 | 0.069 | 51 | 56 |
|   | Bottom | 0.91 | | | | | |
| 7 | Top | 0.94 | 0.026 | 6.05 | 0.087 | 65 | 61 |
|   | Bottom | 0.91 | | | | | |

Practical Example 7

Ion Exchange Amount (Hydrogen Concentration, Na$_2$O Concentration and Sn Concentration) Difference and ΔWarpage Amount Since the hydrogen concentration, Na$_2$O concentration and Sn concentration are considered to be responsible for the ion exchange amount, a correlation formula was determined from the data shown in Table 7 and, as a result, the following formula (6-1) was obtained.

$$\text{Ion exchange amount } 2 = -0.02 \times (H/Si) + 5.54 \times (N-Na_2O \text{ concentration}) - 0.037 \times (Sn \text{ concentration}) \quad \text{formula (6-1)}$$

Since the ion exchange amount difference between the top surface and the bottom surface is considered to affect the Δion exchange amount 2 determined according to formula (6-1), i.e., the difference in the ion exchange amounts 2 between the top surface and the bottom surface, and the warpage of glass after chemical strengthening, the correlation of the Δion exchange amount 2 determined according to formula (6-2), i.e., the difference in the ion exchange amounts 2 between the top surface and the bottom surface, with the Δwarpage amount was examined.

$$\Delta\text{Ion exchange amount } 2 = (\text{ion exchange amount } 2 \text{ in top surface}) - (\text{ion exchange amount } 2 \text{ in bottom surface}) \quad \text{formula (6-2)}$$

FIG. 15 shows a graph plotting, on the abscissa, the difference (Δion exchange amount 2) between ion exchange amounts 2 in top surface and bottom surface, and on the ordinate, Δwarpage amount. The graph shown in FIG. 15 revealed that the Δion exchange amount 2 and the Δwarpage amount have a correlation.

It was understood from the results shown in Table 7 and FIG. 15 that when Δion exchange amount 2 in formula (6-1) is 0.33 or less, the Δwarpage amount can be 58 μm or less.

TABLE 7

| Composition | Example | Surface | H/Si | N—Na$_2$O | SnO$_2$ (μg/cm$^2$) | Ion Exchange Amount 2 | ΔIon Exchange Amount 2 | ΔWarpage Amount (μm) |
|---|---|---|---|---|---|---|---|---|
| A | 1 | Top | 1.02 | 0.94 | 0 | 5.18 | 0.37 | 58 |
|   |   | Bottom | 1.35 | 0.91 | 6.18 | 4.81 | | |
| B | 2 | Top | 1.53 | 0.93 | 0 | 5.12 | 0.29 | 52 |
|   |   | Bottom | 1.60 | 0.91 | 5.46 | 4.83 | | |
|   | 3 | Top | 1.54 | 0.93 | 0 | 5.10 | 0.34 | 60 |
|   |   | Bottom | 1.91 | 0.90 | 5.65 | 4.76 | | |
|   | 4 | Top | 1.23 | 0.92 | 0 | 5.07 | 0.32 | 57 |
|   |   | Bottom | 1.54 | 0.90 | 6.06 | 4.76 | | |
|   | 5 | Top | 1.27 | 0.92 | 0 | 5.05 | 0.38 | 69 |
|   |   | Bottom | 2.02 | 0.89 | 6.13 | 4.66 | | |
|   | 6 | Top | 1.24 | 0.92 | 0 | 5.09 | 0.29 | 56 |
|   |   | Bottom | 1.64 | 0.91 | 5.57 | 4.80 | | |
| C | 7 | Top | 1.10 | 0.94 | 0 | 5.17 | 0.38 | 61 |
|   |   | Bottom | 1.38 | 0.91 | 6.05 | 4.79 | | |

Example 7

Na$_2$O Concentration Difference Between Top Surface and Bottom Surface Before Chemical Strengthening and ΔWarpage Amount Since the Na$_2$O concentration difference between the top surface and the bottom surface of a soda-lime glass sheet before chemical strengthening is considered to have a correlation with the Δwarpage amount, a square [ΔN—Na$_2$O (Top-Bottom)]$^2$ of the difference obtained by subtracting the normalized Na$_2$O surface concentration of the bottom surface from the normalized Na2O surface concentration of the top surface was determined from the data shown in Table 1, and the correlation with the Δwarpage amount was studied.

The results are shown in Table 8 and FIG. 16. In Table 8, for example, "5.9.E-04" means $5.9 \times 10^{-4}$. FIG. 16 is a graph plotting, on the abscissa, a square $[\Delta N - Na_2O \text{ (Top-Bottom)}]^2$ of the difference obtained by subtracting the normalized $Na_2O$ surface concentration of the bottom surface from the normalized $Na_2O$ surface concentration of the top surface to be subjected to chemical strengthening, and on the ordinate, Δwarpage amount.

The graph shown in FIG. 16 revealed that the square $(\Delta N - Na_2O)^2$ of the difference between normalized $Na_2O$ surface concentrations in the top surface and the bottom surface of a soda-lime glass sheet before chemical strengthening and the Δwarpage amount have a correlation represented by the following formula (7-1).

$$\Delta\text{Warpage amount} = 18000 \times (\Delta N - Na_2O)^2 + 51 \quad \text{formula (7-1)}$$

In formula (7-1), the $(\Delta N - Na_2O)^2$ is a square of the difference between the values obtained by measuring, by fluorescent X-ray analysis, the normalized $Na_2O$ surface concentration in the top surface and the bottom surface of glass to be subjected to chemical strengthening and is determined according to the following formula (7-2):

$$(\Delta N - Na_2O)^2 = [(\text{normalized } Na_2O \text{ surface concentration in top surface before chemical strengthening}) - (\text{normalized } Na_2O \text{ surface concentration in bottom surface before chemical strengthening})]^2 \quad \text{formula (7-2)}$$

It was understood from the results shown in Table 8 and FIG. 16 that when $(\Delta N - Na_2O)^2$ in formula (7-1) is $5.0 \times 10^{-4}$ or less, the Δwarpage amount can be 58 μm or less.

TABLE 8

| Example | Surface | N—Na$_2$O | (ΔN—Na$_2$O)^2 | ΔWarpage Amount (μm) |
|---|---|---|---|---|
| 1 | Top | 0.94 | 5.9.E-04 | 58 |
|   | Bottom | 0.91 | | |
| 2 | Top | 0.93 | 2.3.E-04 | 52 |
|   | Bottom | 0.91 | | |
| 3 | Top | 0.93 | 5.4.E-04 | 60 |
|   | Bottom | 0.90 | | |
| 4 | Top | 0.92 | 2.4.E-04 | 57 |
|   | Bottom | 0.90 | | |
| 5 | Top | 0.92 | 6.6.E-04 | 69 |
|   | Bottom | 0.89 | | |
| 6 | Top | 0.92 | 1.7.E-04 | 56 |
|   | Bottom | 0.91 | | |
| 7 | Top | 0.94 | 6.9.E-04 | 61 |
|   | Bottom | 0.91 | | |

[Glass Composition Example]

Composition Examples G1 to G16 in mass % of the float glass for chemical strengthening of the present invention, and the compressive stress CS (unit: MPa) and depth of compressive stress layer DOL (unit: μm) when the float glass was chemically strengthened, are shown in Tables 9 and 10.

In the Tables, $Na_2O/Al_2O_3$ is the ratio of $Na_2O$ and $Al_2O_3$ contents, RO is the total of MgO, CaO, SrO and BaO contents, CaO+SrO+BaO is the total of CaO, SrO and BaO contents, strengthening temperature (unit: ° C.) and strengthening time (unit: h) are those in the chemical strengthening above, $KNO_3$ is the concentration (unit: mass %) of $KNO_3$ in a molten salt used for chemical strengthening, and dol is the dol described above. Here, when the concentration of $KNO_3$ in a molten salt is not 100%, the remaining component is $NaNO_3$.

TABLE 9

|  | G1 | G2 | G3 | G4 | G5 | G6 | G7 | G8 | G9 |
|---|---|---|---|---|---|---|---|---|---|
| SiO$_2$ | 72 | 72 | 72 | 67 | 62 | 60 | 68 | 65.5 | 69 |
| Al$_2$O$_3$ | 2 | 2 | 2 | 1 | 1 | 1 | 5 | 3 | 2 |
| MgO | 4.5 | 4.5 | 4.5 | 6 | 8 | 10 | 5 | 6 | 4 |
| CaO | 8 | 8 | 8 | 9 | 10 | 13 | 7 | 8 | 10 |
| SrO | 0 | 0 | 0 | 0 | 0 | 0 | 1 | 0 | 0 |
| BaO | 0 | 0 | 0 | 0 | 0 | 0 | 0 | 0 | 0 |
| ZrO$_2$ | 0 | 0 | 0 | 0 | 0 | 0 | 0 | 2.5 | 1 |
| Na$_2$O | 13.2 | 13.2 | 13.2 | 15 | 14 | 10 | 13 | 9 | 12 |
| K$_2$O | 0.3 | 0.3 | 0.3 | 2 | 5 | 6 | 1 | 6 | 2 |
| Na$_2$O/Al$_2$O$_3$ | 6.6 | 6.6 | 6.6 | 15.0 | 14.0 | 10.0 | 2.6 | 3.0 | 6.0 |
| RO | 12.5 | 12.5 | 12.5 | 15.0 | 18.0 | 23.0 | 13.0 | 14.0 | 14.0 |
| CaO + SrO + BaO | 8.0 | 8.0 | 8.0 | 9.0 | 10.0 | 13.0 | 8.0 | 8.0 | 10.0 |
| Strengthening temperature | 425 | 425 | 425 | 425 | 425 | 450 | 425 | 425 | 425 |
| Strengthening time t | 2.5 | 2.5 | 2.5 | 2.5 | 2.5 | 5 | 2.5 | 2.5 | 4 |
| KNO$_3$ | 100 | 97.5 | 95 | 100 | 100 | 100 | 100 | 100 | 100 |
| dol | 5 | 5 | 5 | 7 | 6 | 4 | 5 | 5 | 6 |
| CS | 680 | 580 | 480 | 690 | 730 | 810 | 760 | 770 | 710 |
| DOL | 5 | 5 | 5 | 7 | 6 | 4 | 5 | 5 | 6 |

TABLE 10

|  | G10 | G11 | G12 | G13 | G14 | G15 | G16 | G17 | G18 |
|---|---|---|---|---|---|---|---|---|---|
| SiO$_2$ | 65 | 62.5 | 65 | 76.5 | 77.9 | 71 | 74 | 72 | 69 |
| Al$_2$O$_3$ | 5 | 7.5 | 7 | 0.5 | 0.1 | 4 | 4 | 6 | 5 |
| MgO | 6 | 3 | 4 | 3 | 2 | 4 | 3.5 | 4 | 3 |
| CaO | 5 | 6 | 2 | 5 | 4 | 7 | 1.5 | 1 | 1 |
| SrO | 2 | 0 | 1 | 0 | 0 | 0 | 0 | 2 | 0 |
| BaO | 0 | 0 | 1 | 0 | 0 | 0 | 0 | 0 | 2 |
| ZrO$_2$ | 0.2 | 1 | 2 | 0 | 4 | 0 | 0 | 0 | 0 |
| Na$_2$O | 14.3 | 20 | 16.5 | 14 | 12 | 10 | 15 | 11 | 17 |
| K$_2$O | 2.5 | 0 | 1.5 | 1 | 0 | 4 | 2 | 4 | 3 |
| Na$_2$O/Al$_2$O$_3$ | 2.9 | 2.7 | 2.4 | 28.0 | 120 | 2.5 | 3.8 | 1.8 | 3.4 |
| RO | 13.0 | 9.0 | 8.0 | 8.0 | 6.0 | 11.0 | 5.0 | 7.0 | 6.0 |
| CaO + SrO + BaO | 7.0 | 6.0 | 4.0 | 5.0 | 4.0 | 7.0 | 1.5 | 3.0 | 3.0 |
| Strengthening temperature | 425 | 425 | 425 | 425 | 425 | 425 | 400 | 400 | 400 |
| Strengthening time t | 2.5 | 2.5 | 1 | 2.5 | 2.5 | 2.5 | 1 | 1 | 0.5 |
| KNO$_3$ | 100 | 100 | 100 | 100 | 100 | 100 | 100 | 100 | 100 |
| dol | 12 | 20 | 16 | 18 | 10 | 12 | 17 | 12 | 19 |
| CS | 720 | 720 | 730 | 470 | 590 | 630 | 550 | 630 | 560 |
| DOL | 12 | 20 | 16 | 18 | 10 | 12 | 17 | 12 | 19 |

While the present invention has been described in detail with reference to specific embodiments, it is apparent to one skilled in the art that various changes and modifications can be made therein without departing from the intension and scope of the present invention. This application is based on Japanese Patent Application (No. 2012-285511) filed on Dec. 27, 2012, and the whole of which are incorporated by reference.

DESCRIPTION OF REFERENCE NUMERALS AND SIGNS

1 Molten glass
5 Molten metal bath
10 Display device

15 Housing
20 Display panel
30 Cover glass

The invention claimed is:

1. A float glass for chemical strengthening, comprising a bottom surface coming into contact with a molten metal at the time of forming of the float glass and a top surface opposing the bottom surface, wherein a difference $\Delta(N\text{—}Na_2O^2)$ determined by subtracting a square of a normalized $Na_2O$ surface concentration of the bottom surface from a square of a normalized $Na_2O$ surface concentration of the top surface is 0.040 or less, where the normalized $Na_2O$ surface concentration is obtained by dividing an $Na_2O$ concentration in a measured surface, which is the bottom surface or the top surface, by an $Na_2O$ concentration at a depth of 100 μm from the measured surface, where the $Na_2O$ concentration is a value measured by a fluorescent X-ray analysis using an Na—Kα ray.

2. The float glass as claimed in claim 1, wherein W3 determined according to the following formula (5-1) is 58 or less:

$$W3=744\times[(\Delta N\text{—}Na_2O)+0.01\times(\text{Sn concentration difference})] \quad \text{formula (5-1)},$$

wherein, in formula (5-1):
the $\Delta N\text{—}Na_2O$ is a value determined by subtracting the normalized $Na_2O$ surface concentration in the bottom surface from the normalized $Na_2O$ surface concentration in the top surface; and
the Sn concentration difference is a difference obtained by subtracting an Sn deposition amount per unit area (unit: μg/cm²) in the top surface from an Sn deposition amount per unit area (unit: μg/cm²) in the bottom surface, where the Sn deposition amount per unit area is a deposition mass in terms of $SnO_2$ per 1 cm² when Sn is assumed to exist in the form of $SnO_2$.

3. The float glass as claimed in claim 1, wherein Δion exchange amount 2 which is a value obtained by subtracting an ion exchange amount 2 in the bottom surface from an ion exchange amount 2 in the top surface is 0.33 or less,
where the ion exchange amount 2 is a value determined according to the following formula (6-1):

$$\text{Ion exchange amount 2}=-0.02\times(H/Si)+5.54\times(N\text{—}Na_2O\text{ concentration})-0.037\times(\text{Sn concentration}) \quad \text{formula (6-1)},$$

wherein, in formula (6-1):
the H/Si is a normalized hydrogen concentration, where the normalized hydrogen concentration is a value obtained by dividing an average hydrogen concentration at a depth of 0 to 10 μm by an average hydrogen concentration at a depth of 105 to 110 μm, and the average hydrogen concentration at a depth of 0 to 10 μm and the average hydrogen concentration at a depth of 105 to 110 μm are values measured under the following analysis conditions (a) to (i):
(a) Measurement apparatus: secondary ion mass spectrometry apparatus with a quadrupole mass spectrometer,
(b) Primary ion species: $Cs^+$,
(c) Primary accelerating voltage: 5.0 kV,
(d) Primary ion current: 1 μA,
(e) Primary ion incident angle (angle from direction perpendicular to sample surface): 60°,
(f) Luster size: 200×200 μm²,
(g) Detection region: 40×40 μm²,
(h) Secondary ion polarity: minus, and
(i) Electron gun for neutralization: used;

the N—$Na_2O$ concentration is the normalized $Na_2O$ surface concentration; and
the Sn concentration is an Sn deposition amount per unit area(unit: μg/cm²), where the Sn deposition amount is a deposition mass in terms of $SnO_2$ when Sn is assumed to exist in the form of $SnO_2$.

4. The float glass as claimed in claim 1, wherein the float glass is used for chemical strengthening in which a chemical strengthening temperature is T (unit: K) and a chemical strengthening time is t (unit: hours) and contains $SiO_2$, and a dol determined according to the following formula by using respective contents in mass % of $SiO_2$, $Al_2O_3$, MgO, CaO, SrO, BaO, $ZrO_2$, $Na_2O$ and $K_2O$ is 20 or less:

$$dol=-0.13\times Al_2O_3-1.88\times MgO-2.41\times CaO-1.85\times SrO-1.35\times BaO-1.59\times ZrO_2+1.50\times Na_2O+2.42\times K_2O-129359/T+9.28\times t^{0.5}+182.88.$$

5. The float glass as claimed in claim 1, comprising: in mass %, from 60 to 80% of $SiO_2$, from 0 to 8% of $Al_2O_3$, from 8 to 22% of $Na_2O$, from 0 to 7% of $K_2O$, from 0 to 17% of MgO, from 0 to 22% of CaO, from 0 to 8% of SrO, from 0 to 8% of BaO, and from 0 to 5% of $ZrO_2$.

6. The float glass as claimed in claim 5, comprising at least one of CaO, SrO and BaO, wherein the total of the CaO, SrO and BaO contents is from 1 to 7%.

7. The float glass as claimed in claim 1, comprising: in mass %, from 60 to 80% of $SiO_2$, from 0.01 to 8% of $Al_2O_3$, from 8 to 22% of $Na_2O$, from 0 to 7% of $K_2O$ and from 0 to 5% of $ZrO_2$, wherein in the case where at least one of MgO, CaO, SrO and BaO is contained in the float glass, the total of the MgO, CaO, SrO and BaO contents is from 5 to 25%, and a ratio of the $Na_2O$ content to the $Al_2O_3$ content ($Na_2O/Al_2O_3$) is 1.5 or more.

8. The float glass as claimed in claim 7, wherein the ratio $Na_2O/Al_2O_3$ is 6 or less.

9. A method for producing a chemically strengthened glass having a depth of compressive stress layer of 20 μm or less, comprising chemically strengthening the float glass as claimed in claim 1.

10. A float glass for chemical strengthening, comprising a bottom surface coming into contact with a molten metal at the time of forming of the float glass and a top surface opposing the bottom surface, wherein a Δion exchange amount 1 which is a value obtained by subtracting an ion exchange amount 1 in the bottom surface from an ion exchange amount 1 in the top surface is 0.32 or less,
where the ion exchange amount 1 is a value determined according to the following formula (2-1):

$$\text{Ion exchange amount 1}=5.51\times(\text{normalized }Na_2O\text{ surface concentration})-0.038\times(\text{Sn concentration}) \quad \text{formula (2-1)},$$

wherein, in formula (2-1):
the normalized $Na_2O$ surface concentration is a value obtained by dividing an $Na_2O$ concentration at a measured surface, which is the bottom surface or the top surface, by an $Na_2O$ concentration at a depth position of 100 μm from the measured surface, where the $Na_2O$ concentration is a value measured by a fluorescent X-ray analysis using an Na—Kα ray; and
the Sn concentration is an Sn deposition amount per unit area (unit: μg/cm²) in the measured surface, where the Sn deposition amount per unit area is a deposition mass in terms of $SnO_2$ per 1 cm² when Sn is assumed to exist in the form of $SnO_2$.

11. The float glass as claimed in claim 10, wherein W3 determined according to the following formula (5-1) is 58 or less:

$$W3=744\times[(\Delta N\text{—}Na_2O)+0.01\times(Sn\text{ concentration difference})] \quad \text{formula (5-1)},$$

wherein, in formula (5-1):
the $\Delta N$—$Na_2O$ is a value determined by subtracting the normalized $Na_2O$ surface concentration in the bottom surface from the normalized $Na_2O$ surface concentration in the top surface; and
the Sn concentration difference is a difference obtained by subtracting an Sn deposition amount per unit area (unit: $\mu g/cm^2$) in the top surface from an Sn deposition amount per unit area (unit: $\mu g/cm^2$) in the bottom surface.

12. The float glass as claimed in claim 10, wherein $\Delta$ion exchange amount 2 which is a value obtained by subtracting an ion exchange amount 2 in the bottom surface from an ion exchange amount 2 in the top surface is 0.33 or less,
where the ion exchange amount 2 is a value determined according to the following formula (6-1):

$$\text{Ion exchange amount 2}=-0.02\times(H/Si)+5.54\times(N\text{—}Na_2O\text{ concentration})-0.037\times(Sn\text{ concentration}) \quad \text{formula (6-1)},$$

wherein, in formula (6-1):
the H/Si is a normalized hydrogen concentration, where the normalized hydrogen concentration is a value obtained by dividing an average hydrogen concentration at a depth of 0 to 10 $\mu$m by an average hydrogen concentration at a depth of 105 to 110 $\mu$m, and the average hydrogen concentration at a depth of 0 to 10 $\mu$m and the average hydrogen concentration at a depth of 105 to 110 $\mu$m are values measured under the following analysis conditions (a) to (i):
(a) Measurement apparatus: secondary ion mass spectrometry apparatus with a quadrupole mass spectrometer,
(b) Primary ion species: $Cs^+$,
(c) Primary accelerating voltage: 5.0 kV,
(d) Primary ion current: 1 $\mu$A,
(e) Primary ion incident angle (angle from direction perpendicular to sample surface): 60°,
(f) Luster size: 200×200 $\mu m^2$,
(g) Detection region: 40×40 $\mu m^2$,
(h) Secondary ion polarity: minus, and
(i) Electron gun for neutralization: used;
the N—$Na_2O$ concentration is the normalized $Na_2O$ surface concentration; and
the Sn concentration is as defined in formula (2-1).

13. A float glass for chemical strengthening, comprising a bottom surface coming into contact with a molten metal at the time of forming of the float glass and a top surface opposing the bottom surface, wherein W1 determined according to the following formula (3-1) is 56 or less:

$$W1=-16\times(\Delta H/Si)-6.47\times(Sn\text{ concentration difference})-43.8\times(\Delta\text{ion exchange amount 1}) \quad \text{formula (3-1)},$$

wherein, in formula (3-1):
the $\Delta H/Si$ is a value obtained by subtracting a normalized hydrogen concentration in the bottom surface from a normalized hydrogen concentration in the top surface, where the normalized hydrogen concentration is a value obtained by dividing an average hydrogen concentration at a depth of 0 to 10 $\mu$m by an average hydrogen concentration at a depth of 105 to 110 $\mu$m, and the average hydrogen concentration at a depth of 0 to 10 $\mu$m and the average hydrogen concentration at a depth of 105 to 110 $\mu$m are values measured under the following analysis conditions (a) to (i):
(a) Measurement apparatus: secondary ion mass spectrometry apparatus with a quadrupole mass spectrometer,
(b) Primary ion species: $Cs^+$,
(c) Primary accelerating voltage: 5.0 kV,
(d) Primary ion current: 1 $\mu$A,
(e) Primary ion incident angle (angle from direction perpendicular to sample surface): 60°,
(f) Luster size: 200×200 $\mu m^2$,
(g) Detection region: 40×40 $\mu m^2$,
(h) Secondary ion polarity: minus, and
(i) Electron gun for neutralization: used;
the Sn concentration difference is a difference obtained by subtracting an Sn deposition amount per unit area (unit: $\mu g/cm^2$) in the top surface from an Sn deposition amount per unit area (unit: $\mu g/cm^2$) in the bottom surface, where the Sn deposition amount per unit area is a deposition mass in terms of $SnO_2$ per 1 $cm^2$ when Sn is assumed to exist in the form of $SnO_2$; and
the $\Delta$ion exchange amount 1 is a value obtained by subtracting an ion exchange amount 1 in the bottom surface from an ion exchange amount 1 in the top surface, where the ion exchange amount 1 is determined according to the following formula:

$$\text{Ion exchange amount 1}=5.51\times(\text{normalized }Na_2O\text{ surface concentration})-0.038\times(Sn\text{ concentration}),$$

wherein the normalized $Na_2O$ surface concentration is a value obtained by dividing an $Na_2O$ concentration at a measured surface, which is the bottom surface or the top surface, by an $Na_2O$ concentration at a depth position of 100 $\mu$m from the measured surface, where the $Na_2O$ concentration is a value measured by a fluorescent X-ray analysis using an Na—K$\alpha$ ray.

14. The float glass as claimed in claim 13, wherein W3 determined according to the following formula (5-1) is 58 or less:

$$W3=744\times[(\Delta N\text{—}Na_2O)+0.01\times(Sn\text{ concentration difference})] \quad \text{formula (5-1)},$$

wherein, in formula (5-1):
the $\Delta N$—$Na_2O$ is a value determined by subtracting the normalized $Na_2O$ surface concentration in the bottom surface from the normalized $Na_2O$ surface concentration in the top surface; and
the Sn concentration difference is as defined in formula (3-1).

15. The float glass as claimed in claim 13, wherein $\Delta$ion exchange amount 2 which is a value obtained by subtracting an ion exchange amount 2 in the bottom surface from an ion exchange amount 2 in the top surface is 0.33 or less,
where the ion exchange amount 2 is a value determined according to the following formula (6-1):

$$\text{Ion exchange amount 2}=-0.02\times(H/Si)+5.54\times(N\text{—}Na_2O\text{ concentration})-0.037\times(Sn\text{ concentration}) \quad \text{formula (6-1)},$$

wherein, in formula (6-1):
the H/Si is the normalized hydrogen concentration;
the N—$Na_2O$ concentration is the normalized $Na_2O$ surface concentration; and
the Sn concentration is the Sn deposition amount per unit area.

16. A float glass for chemical strengthening, comprising a bottom surface coming into contact with a molten metal at the time of forming of the float glass and a top surface opposing the bottom surface, wherein an absolute value of W2 determined according to the following formula (4-1) is 56 or less:

$$W2 = 9.18 \times \Delta[(\text{ion exchange amount 1})/(H/Si)] + 49 \quad \text{formula (4-1)},$$

wherein, in formula (4-1):

the $\Delta[(\text{ion exchange amount 1})/(H/Si)]$ is a value determined by subtracting a value obtained by dividing an ion exchange amount 1 in the bottom surface by a normalized hydrogen concentration H/Si in the bottom surface, from a value obtained by dividing an ion exchange amount 1 in the top surface by a normalized hydrogen concentration H/Si in the top surface, where the ion exchange amount 1 is determined according to the following formula:

$$\text{Ion exchange amount 1} = 5.51 \times (\text{normalized Na}_2\text{O surface concentration}) - 0.038 \times (\text{Sn concentration}),$$

in the formula, the normalized $Na_2O$ surface concentration is a value obtained by dividing an $Na_2O$ concentration at a measured surface, which is the bottom surface or the top surface, by an $Na_2O$ concentration at a depth position of 100 μm from the measured surface, where the $Na_2O$ concentration is a value measured by a fluorescent X-ray analysis using an Na—Kα ray, and the Sn concentration is an Sn deposition amount per unit area (unit: μg/cm$^2$) of the measured surface, where the Sn deposition amount per unit area is a deposition mass in terms of $SnO_2$ per 1 cm$^2$ when Sn is assumed to exist in the form of $SnO_2$; and where the normalized hydrogen concentration is a value obtained by dividing an average hydrogen concentration at a depth of 0 to 10 μm by an average hydrogen concentration at a depth of 105 to 110 μm, and the average hydrogen concentration at a depth of 0 to 10 μm and the average hydrogen concentration at a depth of 105 to 110 μm are values measured under the following analysis conditions (a) to (i):

(a) Measurement apparatus: secondary ion mass spectrometry apparatus with a quadrupole mass spectrometer,
(b) Primary ion species: $Cs^+$,
(c) Primary accelerating voltage: 5.0 kV,
(d) Primary ion current: 1 μA,
(e) Primary ion incident angle (angle from direction perpendicular to sample surface): 60°,
(f) Luster size: 200×200 μm$^2$,
(g) Detection region: 40×40 μm$^2$,
(h) Secondary ion polarity: minus, and
(i) Electron gun for neutralization: used.

17. The float glass as claimed in claim 16, wherein W3 determined according to the following formula (5-1) is 58 or less:

$$W3 = 744 \times [(\Delta N - Na_2O) + 0.01 \times (\text{Sn concentration difference})] \quad \text{formula (5-1)},$$

wherein, in formula (5-1):

the $\Delta N - Na_2O$ is a value determined by subtracting the normalized $Na_2O$ surface concentration in the bottom surface from the normalized $Na_2O$ surface concentration in the top surface; and the Sn concentration difference is a difference obtained by subtracting an Sn deposition amount per unit area (unit: μg/cm$^2$) in the top surface from an Sn deposition amount per unit area (unit: μg/cm$^2$) in the bottom surface.

18. The float glass as claimed in claim 16, wherein Δion exchange amount 2 which is a value obtained by subtracting an ion exchange amount 2 in the bottom surface from an ion exchange amount 2 in the top surface is 0.33 or less, where the ion exchange amount 2 is a value determined according to the following formula (6-1):

$$\text{Ion exchange amount 2} = -0.02 \times (H/Si) + 5.54 \times (N - Na_2O \text{ concentration}) - 0.037 \times (\text{Sn concentration}) \quad \text{formula (6-1)},$$

wherein, in formula (6-1):

the H/Si is the normalized hydrogen concentration;
the $N - Na_2O$ concentration is the normalized $Na_2O$ surface concentration; and
the Sn concentration is as defined in the formula of Ion exchange amount 1.

* * * * *